(12) United States Patent
Bechtold et al.

(10) Patent No.: US 6,241,709 B1
(45) Date of Patent: **\*Jun. 5, 2001**

(54) INJECTION DEVICE

(75) Inventors: Herbert Bechtold, Ehningen; Jochen Gabriel, Stuttgart, both of (DE)

(73) Assignee: B D Medico S.a.r.l., Mies (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,289

(22) PCT Filed: May 29, 1995

(86) PCT No.: PCT/EP95/02032

§ 371 Date: Dec. 2, 1996

§ 102(e) Date: Dec. 2, 1996

(87) PCT Pub. No.: WO95/32749

PCT Pub. Date: Dec. 7, 1995

(30) Foreign Application Priority Data

May 30, 1994 (DE) .................................................. 44 18 824

(51) Int. Cl.$^7$ ............................................. A61M 5/00
(52) U.S. Cl. ...................... 604/207; 604/208; 604/211; 604/232
(58) Field of Search ................... 604/187, 218, 604/207–211, 224, 232, 71, 72, 134, 136, 138, 156, 181

(56) References Cited

U.S. PATENT DOCUMENTS

| | | |
|---|---|---|
| 2,695,023 | 11/1954 | Brown . |
| 4,659,327 | 4/1987 | Bennett et al. ...................... 604/134 |
| 4,865,591 | 9/1989 | Sams ..................................... 604/186 |
| 4,883,472 | 11/1989 | Michel .................................. 604/208 |
| 4,973,318 | 11/1990 | Holm et al. .......................... 604/208 |
| 5,114,406 | 5/1992 | Gabriel et al. ....................... 604/136 |
| 5,304,152 | * 4/1994 | Sams .................................... 604/207 |
| 5,480,387 | * 1/1996 | Gabriel et al. ....................... 604/134 |
| 5,514,097 | 5/1996 | Knauer ................................. 604/136 |
| 5,611,783 | * 3/1997 | Mikkelsen ............................ 604/208 |
| 5,643,214 | * 7/1997 | Marshall et al. ..................... 604/134 |
| 5,984,900 | * 11/1999 | Mikkelsen ............................ 604/208 |

FOREIGN PATENT DOCUMENTS

| | | |
|---|---|---|
| 2 155 575 | 8/1994 | (CA) . |
| 2 056 688 | 3/1972 | (DE) . |
| 0498737 | * 8/1992 | (EP) . |
| WO91/10460 | 7/1991 | (WO) . |
| WO94/17846 | 8/1994 | (WO) . |
| WO94/26331 | 11/1994 | (WO) . |

OTHER PUBLICATIONS

Paul Cutler, *Deferoxamine Therapy in High–Ferritin Diabetes,* "Diabetes" (1989), vol. 38, pp. 1207–1210.

* cited by examiner

*Primary Examiner*—Angela D. Sykes
*Assistant Examiner*—Patricia M Blanco
(74) *Attorney, Agent, or Firm*—Milton, Oliver, Ware, Fressola, Van Der Sluys & Adolphson LLP

(57) ABSTRACT

The invention relates to an injection device (10) having a housing (15) and an injection fluid container (12) which can move, in relation to this housing, between a distal and proximal end position, and also having a pushrod (14) to act on a plunger (23) in this container (12) for the purpose of expelling fluid from the container. A drive connection (27) is provided between the pushrod (14) and the container (12) and, in the distal end position of the container, this drive connection is effective in both the proximal and the distal direction, but in the proximal end position of the container (12), it is only effective when the pushrod (14) is moved in the distal direction.

43 Claims, 17 Drawing Sheets

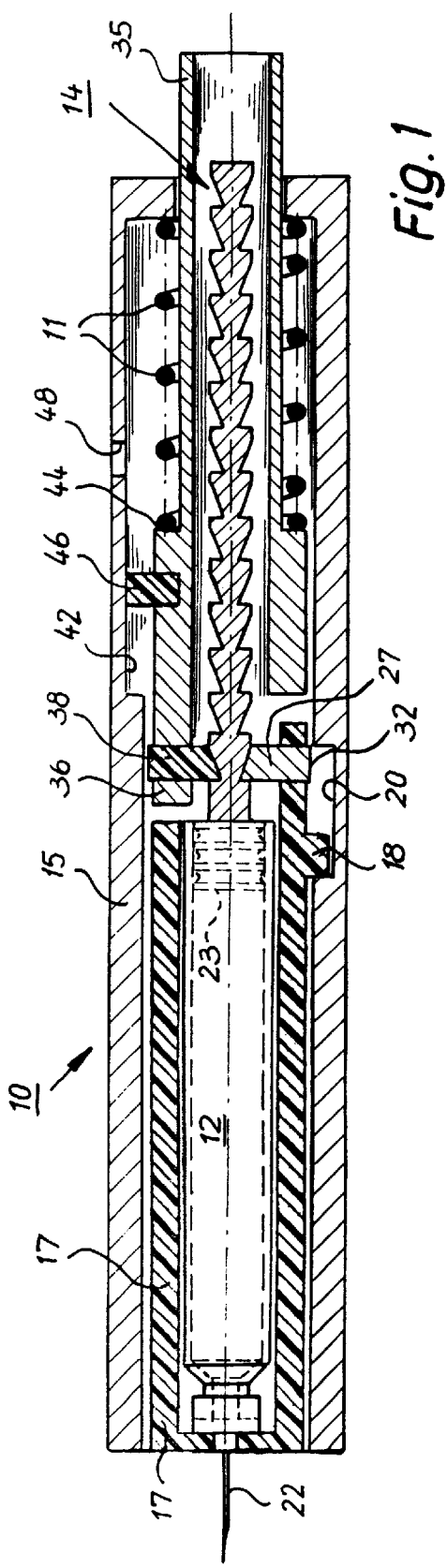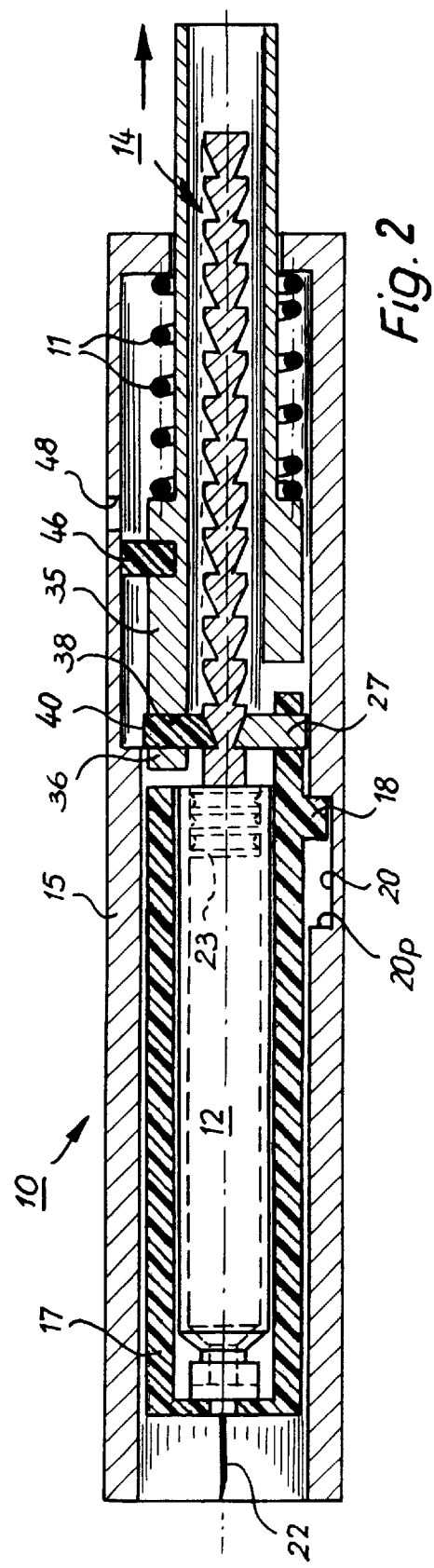

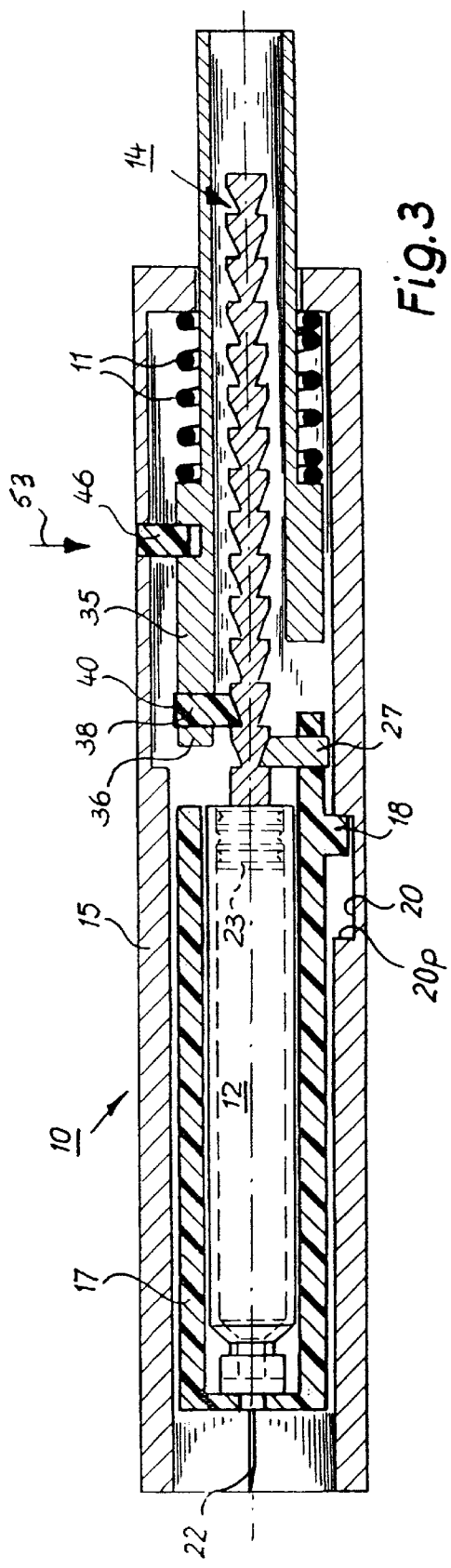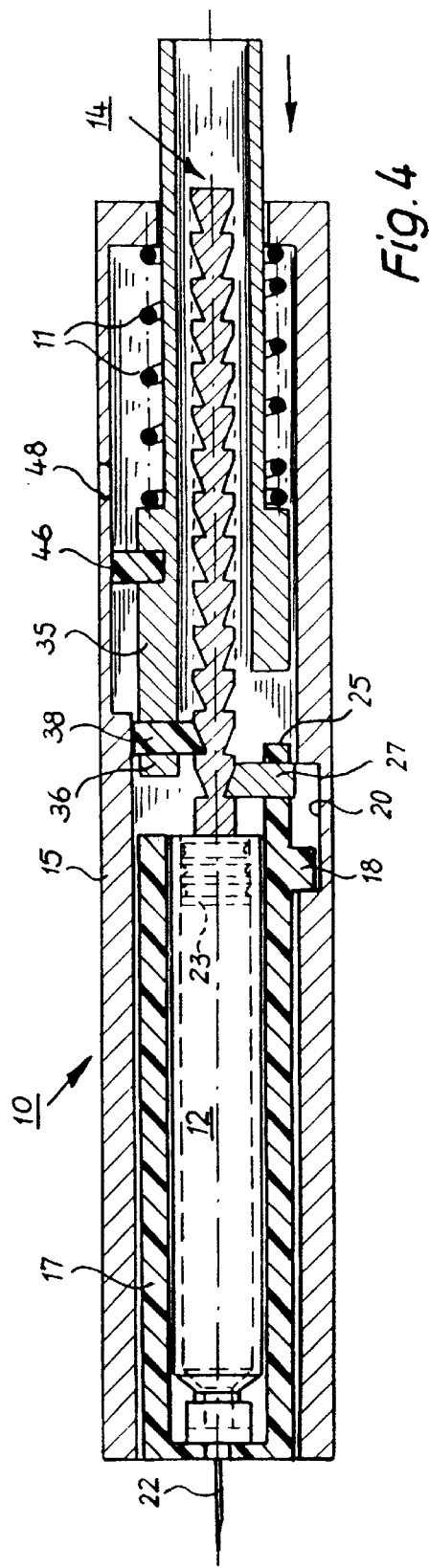

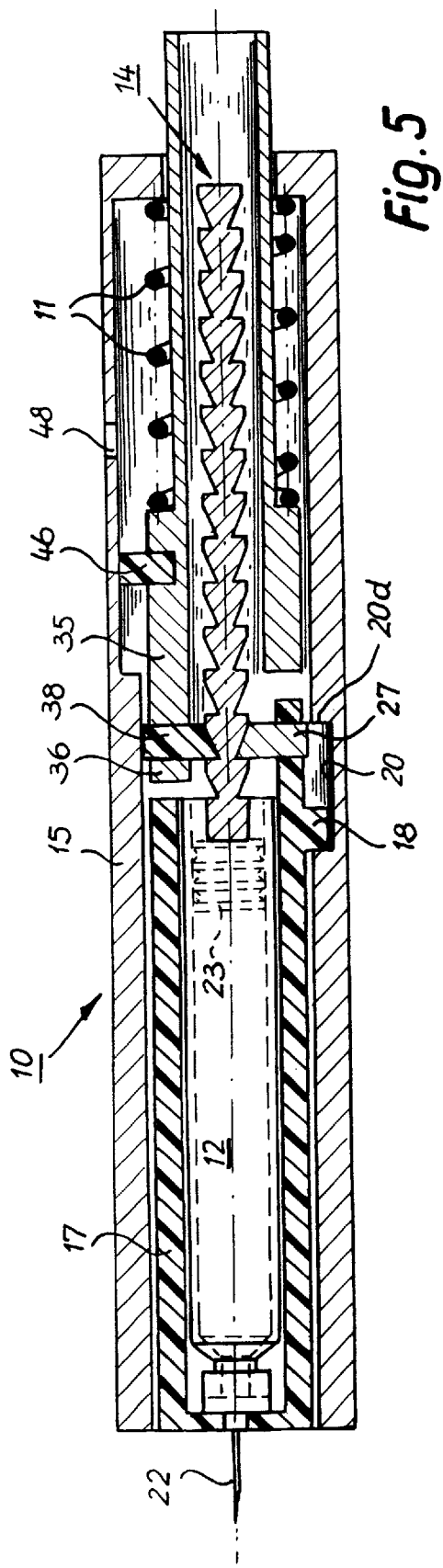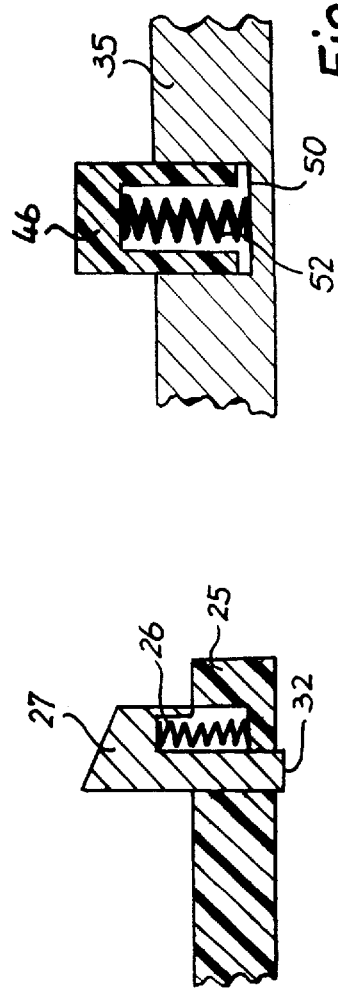

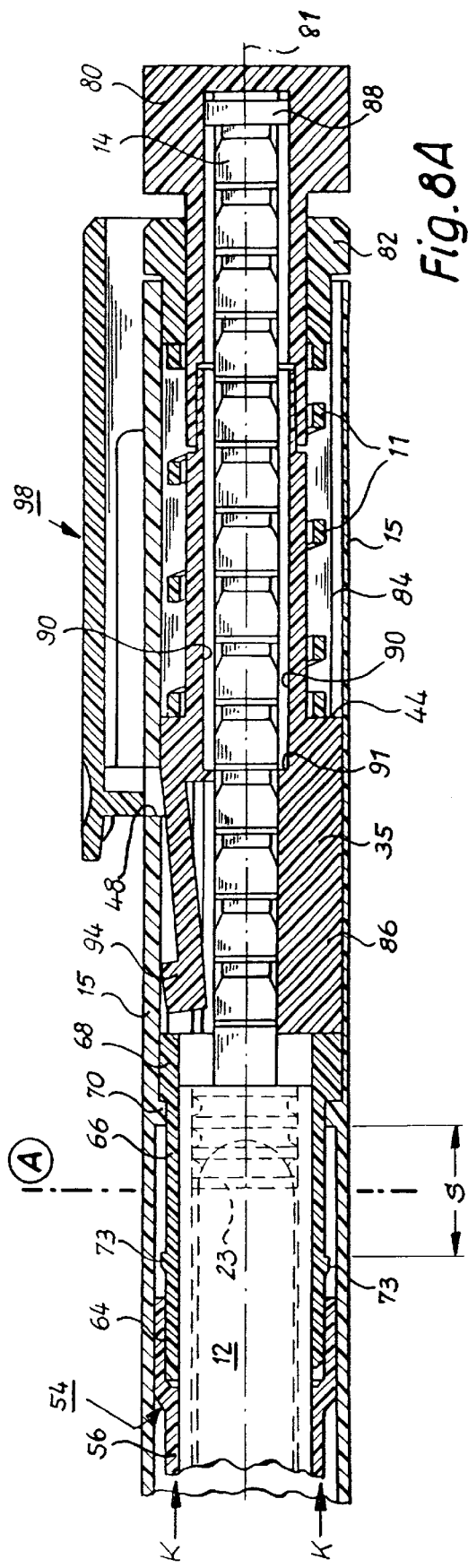
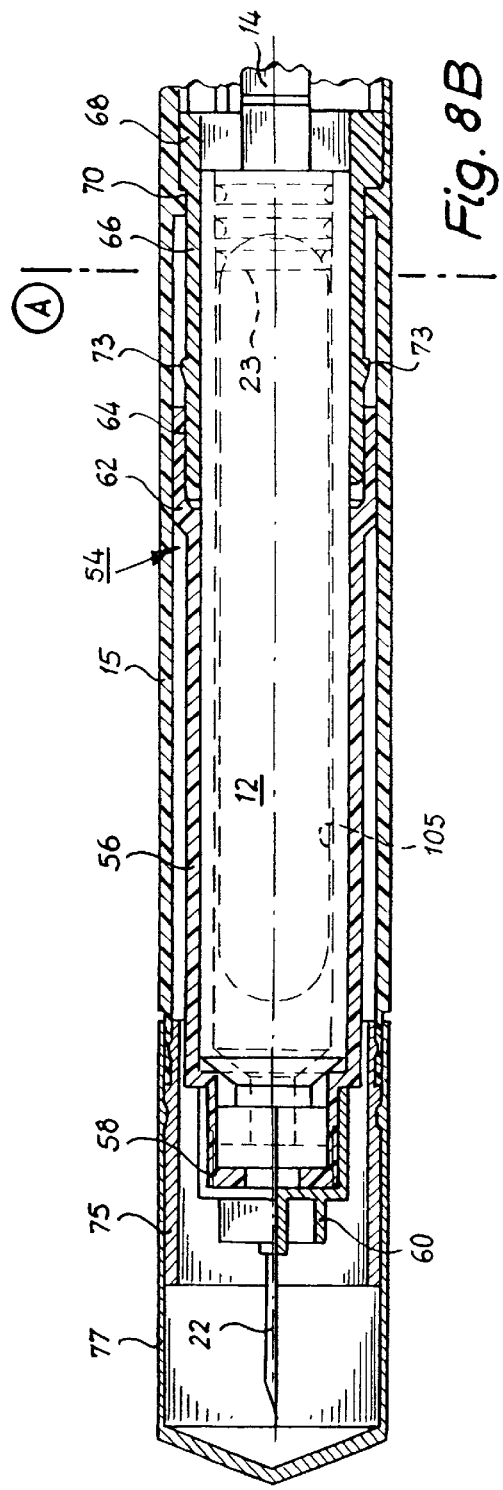

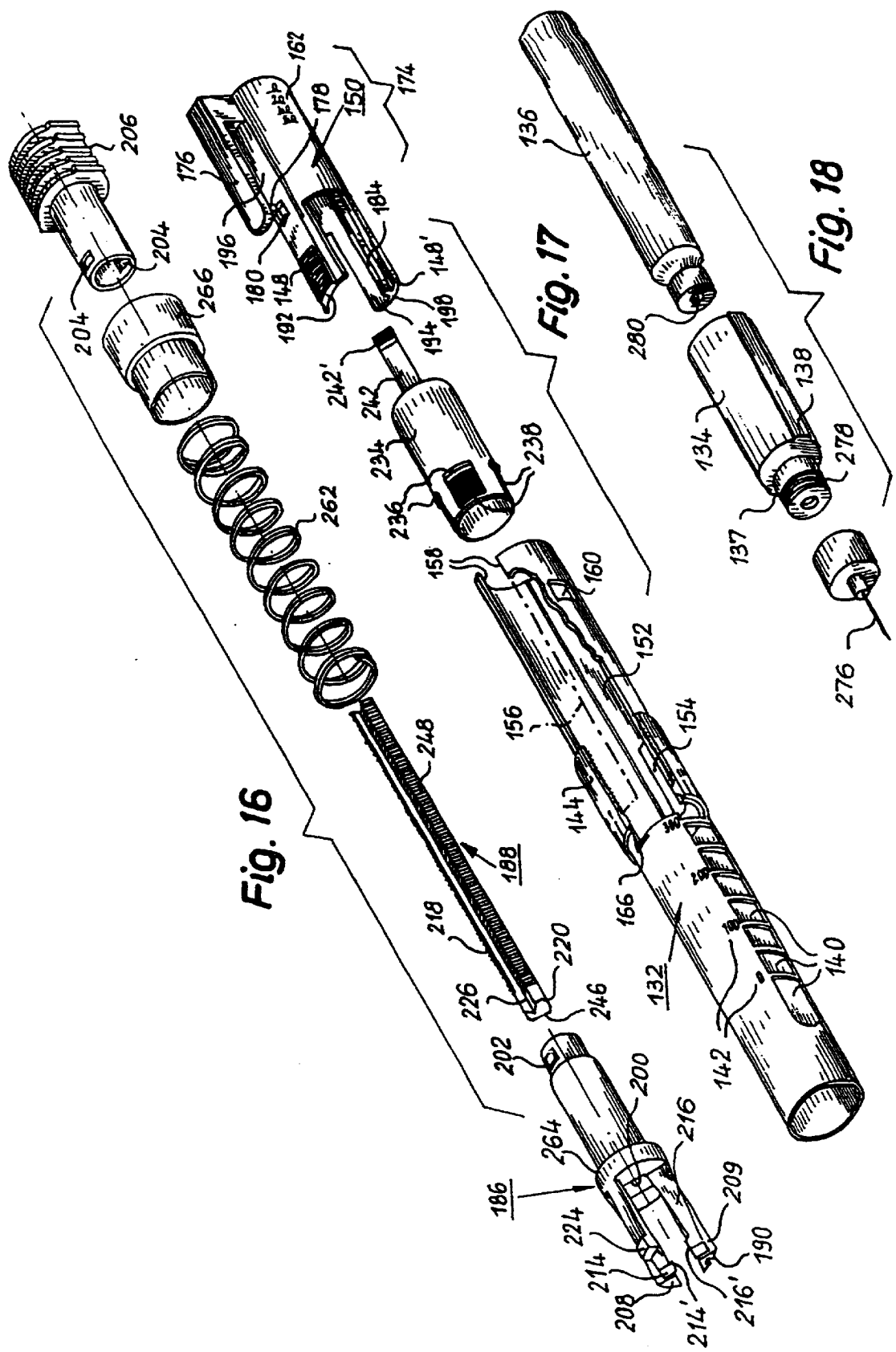

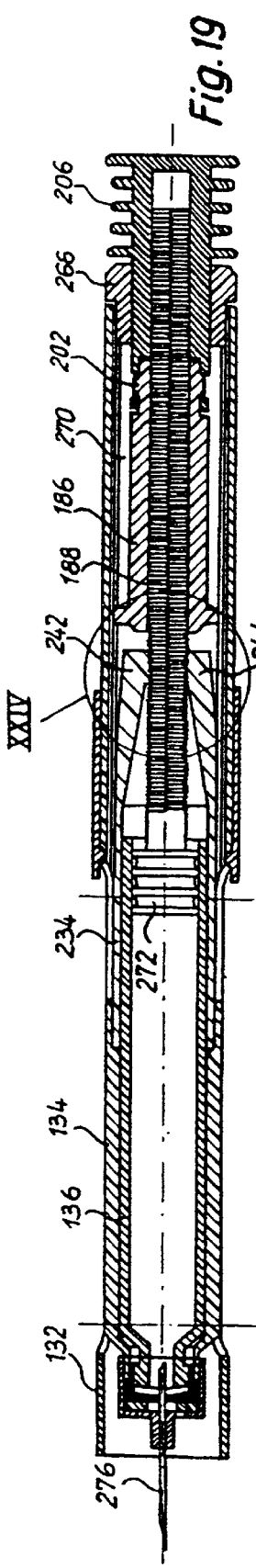
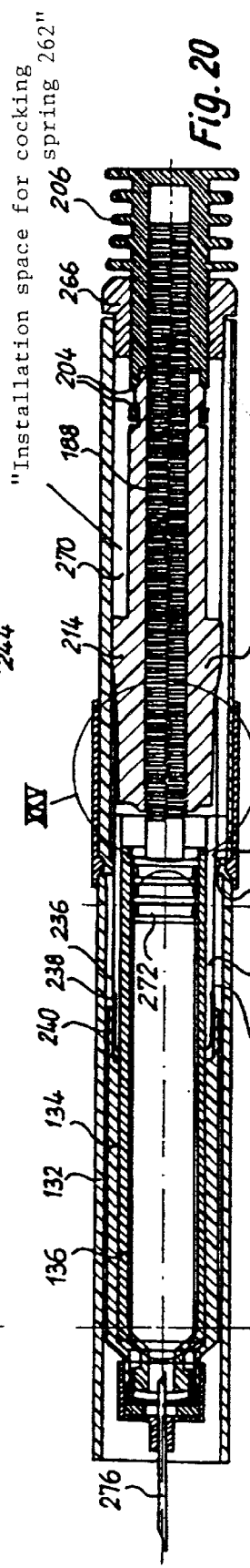
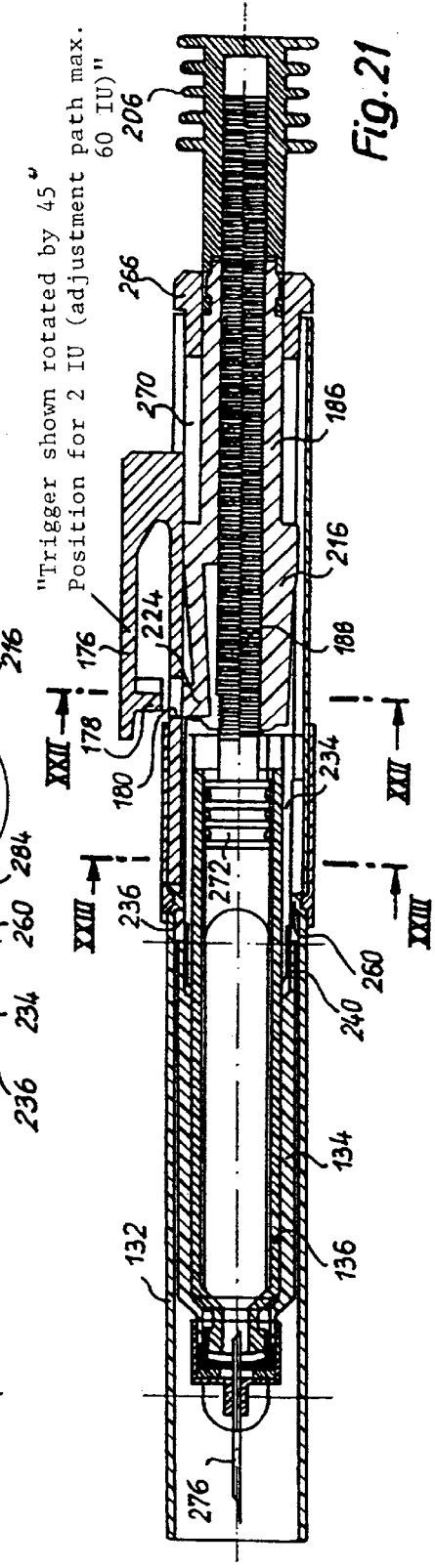

INJECTION DEVICE

The invention relates to an injection device that can preferably administer a number of injections from the contents of a container in the injection device. For example, this kind of injection device is used by patients with pernicious anemia in order to give themselves regular injections of hydroxycobalamin.

In devices of this kind that are used by laymen, it is important that the operation is simple and easy to understand, and that the injection does not cause much pain. It is also desirable that the patient who has a particular fear of needles does not see the needle directly.

BACKGROUND

A great number of semi-automatic and fully automatic injection devices have been disclosed. Their construction is often very complex so that manufacturing costs are high. If after being used, a device is not intended for reuse but for disposal or recycling, then a device of this kind has to be composed of few parts and be very cheap to manufacture. Most injection devices which operate semi-automatically or fully automatically do not meet this demand. See for example the fully automatic injection devices according to DE 39 14 818-A1, DE 40 13 769-A1, or DE-UM 92 00 192 (all by Adamaszek). These devices require a first spring for the insertion of the needle and a second spring for the injection of the fluid, and furthermore, corresponding control devices that trigger the injection process by means of the second spring only when the insertion of the needle is finished, as a result of which these devices become very complex and expensive.

It is a task or objective of the invention to provide a new injection device.

SUMMARY OF THE INVENTION

This object is achieved according to the invention by an injection device comprising a housing and an injection fluid container which is displaceable in relation to this housing, between a distal and a proximal end position. The device also comprises a pushrod movable, in relation to the housing, to expel fluid from the container. A first connecting device, which acts in a position-dependent and/or direction-dependent manner, is provided between the pushrod and the container. The connecting device between the pushrod and the container is thus preferably a controlled connecting device, i.e. the container follows the motion of the pushrod only when it is logical and required for the operation of the device. Preferably, this connecting device is controlled by the position of the container relative to the housing.

In a movement of the pushrod in the distal direction, the first connecting device is advantageously adapted to produce a unidirectional, positive connection between the pushrod and the container and to move the latter along with the pushrod in the distal direction, and it is furthermore so formed to convert a movement of the pushrod in the proximal direction into a corresponding movement of the container in the proximal direction as long as the container is not prevented from moving in the proximal direction in the housing. Therefore, during a distal movement, the pushrod is positively coupled to the container, that is, their movements are "positively synchronized", but a proximal movement of the pushrod will move the container only until it has reached its proximal end position in the housing, for example, whereafter the proximal movement of the pushrod will occur independently of the container, in order to expel fluid from the container.

Suitably, the unidirectional, positive connection is formed so that an abutment for the distal movement of the container also constitutes a limitation for the distal movement of the pushrod. Thus, if the container reaches its distal end position, then a further movement of the pushrod in the distal direction is prevented.

According to another embodiment of the invention, in the distal end position of the container, the first connecting device acts in both the proximal and the distal direction, but in the proximal end position of the container, it is only effective when the pushrod moves in the distal direction. This produces reliable operation having a simple structure.

Another very preferable embodiment of the invention relates to an injection device which has a drive mechanism for the pushrod and a second connecting device provided between the drive mechanism and the pushrod and acting in a path dependent or direction-dependent manner. The second connecting device is thus preferably a controlled connecting device, that is, the pushrod follows the movement of the drive mechanism only when it is logical and required for the operation of the device. Preferably the second connecting device is controlled by the position of the container in relation to the housing, too.

The second connecting device is also very advantageously adapted to produce a unidirectional, positive connection between the drive mechanism and the pushrod when the drive mechanism is moved in the proximal direction and to move the pushrod along with the drive mechanism in the proximal direction and to convert a movement of the drive mechanism in the distal direction into a corresponding movement of the pushrod in the distal direction as long as the pushrod is not prevented from moving in the distal direction. This has turned out to be very advantageous for the operation of the device, and a relative movement between the drive mechanism and pushrod permits a simple adjustment of the dosage to be injected.

Also, in a proximal position region of the container, the second connecting device advantageously produces a connection between the drive mechanism and the pushrod in both the proximal and the distal direction. After an injection, this makes it possible to bring the container into its distal end position.

A further advantageous embodiment of the second drive connection is characterized in that in a distal position region of the container, this second drive connection produces a connection between the drive mechanism and the pushrod, which is effective in the proximal direction and permits the drive mechanism to move in the distal direction relative to the pushrod. After the distal end position of the container is reached, this makes it possible to displace the drive mechanism in the distal direction relative to the pushrod and in this way, to set an injection dosage since the combined length of the drive mechanism and the pushrod will increase as a result.

A fully automatic injection is permitted in a simple manner with such an injection device wherein the drive mechanism is associated with a spring and a detent mechanism; the spring, which in particular is a spring made of plastic material, acts on the drive mechanism in the proximal direction and can be compressed by sliding the detent mechanism in the distal direction where the detent mechanism engages when it reaches a predetermined cocked position. In its cocked position, the spring thus permits a fully automatic injection process via the second and the first connecting device. Because of the energy stored in this spring after being compressed, first a needle connected to the container is inserted and then the fluid is expelled from the container and injected. This permits the manufacture of a very simple, fully-automatic injector made of few parts. However, a device of this kind can also be actuated manually, that is, without a spring, wherein the user first inserts the needle by actuating a single actuation member and then injects the fluid in the set quantity.

In a very simple embodiment, the pushrod is formed, at least in some regions, in the form of a toothed rod. Such a toothed rod is easy and cheap to make, e.g., out of synthetic material. The teeth of the toothed rod are advantageously formed so that they only permit a movement of the toothed rod in the proximal direction in relation to a resilient detent mechanism. The pushrod is also advantageously associated with an abutment which at least limits its proximal movement in relation to the housing. By means of this, the user can see it when the fluid quantity in the container has been used up, or in this case, the device prevents further injection procedures in which no more fluid could be injected.

The container is advantageously associated with a retainer which receives the container and is displaceable axially in the housing between a proximal and a distal end position. This protects the container and makes it possible to insert it into the injection device towards the end of manufacture, which is desirable for sterile manufacturing.

According to an extraordinarily advantageous embodiment of the invention, the length of the retainer is adjustable. This permits the necessary adjusting procedures because the containers are in fact fixed in size, but always have manufacturing tolerances, as does the plunger usually disposed in them, and these tolerances can be compensated for in a simple way by adjusting the length of the retainer. To that end, the retainer advantageously has a proximal section and a distal section which are connected to each other by an adjustable connection which permits a change and in particular a shortening of the overall length of the retainer, for example by means of an axial force, particularly through the use of a micro-detent mechanism. A micro-detent mechanism of this kind, or for example a corresponding screw connection with a fine pitch thread, permits a fine adjustment of the length of the retainer and hence a very exact adjustment, as is desired for an exact maintenance of the injection dosage.

In its proximal end position, the retainer advantageously abuts with its distal end against a proximal end section of the drive member. This permits a simple fine adjustment by means of an axial force, which acts on the proximal end of the retainer, for example, and makes a micro-detent mechanism shift.

Another solution to the task presented is achieved by an injection device having a housing, comprising an injection fluid container disposed in this housing, further comprising a pushrod movable in relation to the housing to expel fluid from this container, further comprising a retainer serving to hold the container and movable in the housing between a proximal and a distal end position, and comprising a device for adjusting the length of this retainer. An embodiment of this kind permits a simple manufacture and final adjustment of an injection device of this kind.

An extraordinarily advantageous improvement of the invention relates to an injection device in which the housing is formed of at least two parts and a device is provided for changing the relative position of these housing parts, in particular by means of linear relative displacement. In a simple way, this permits an adjustment of the injection dosage, in particular if a first housing part is provided for guiding the retainer that receives the injection fluid container and a second housing part that is displaceable in relation to the first one has detent means for engaging with a detent mechanism provided on the drive mechanism. Since in this manner, the detent means can change its position in relation to the housing, the distance that the drive mechanism covers until it engages can be changed and this means that the user can vary the injection dosage by displacing the part with the detent means in relation to the other housing part.

A further refinement of the invention relates to an injection device in which the rows of teeth on the opposite sides of a toothed rod serving as the pushrod, and/or the teeth on elements elastically engaged with these rows of teeth, are axially offset in relation to each other in order to alternatively permit the teeth of the first of two resilient elements to completely engage with the row of teeth associated with it, or to permit the teeth of the second of two resilient elements to completely engage with the row of teeth associated with it on the pushrod, and in this way, to permit the injection device to be more finely adjusted. This turns out to be particularly advantageous when the intent is to set very small injection dosages, which correspond to movements of the plunger in a cartridge, which movements are shorter than 1 mm.

BRIEF FIGURE DESCRIPTION

Further details and advantageous improvements of the invention are revealed in the exemplary embodiments described below and shown in the drawings. These exemplary embodiments are in no way to be understood as limitations of the invention.

FIGS. 1 to 5 are diagrams which represent the chronological course of an injection procedure in schematic form, FIGS. 6 and 7 are graphic explanations of details from FIGS. 1 to 5, FIGS. 8A and 8B show a longitudinal section through a preferred embodiment of an injection device according to the invention, when in the uncocked state, FIGS. 9A and 9B are representations analogous to FIG. 8, but in the cocked state, FIG. 10 is a schematic, three-dimensional representation of the proximal end of the pushrod used in the first and second exemplary embodiment, in the form of a toothed rod with an approximately square cross section, FIGS. 11A and 11B show a longitudinal section analogous to FIGS. 8 and 9, but in a plane perpendicular to these two Figures, FIG. 12 shows how a hook of a connecting device engages in the pushrod of FIG. 10, FIG. 13 is an enlarged schematic representation of the detent mechanism between parts of the retainer 54, as also used in the third embodiment below, FIG. 14 is a three-dimensional representation of an injection device according to a third embodiment of the invention in which the injection dosage can be adjusted, FIG. 15 is a three-dimensional representation analogous to FIG. 14, but for a better view, the housing is shown in a partial cutaway view and in the region of this cutaway, the internal parts of the injection device are not shown, FIG. 16 is a three-dimensional exploded view of internal parts of the injection device of FIGS. 14 and 15, FIG. 17 is a three-dimensional exploded view of the housing of FIGS. 14 and 15 and a retainer part disposed in it, FIG. 18 is a three-dimensional exploded view of a cartridge, its retainer, and an injection needle, FIGS. 19 to 21 are various representations of the injection device according to the third embodiment in longitudinal section and in various positions; the cocking spring is not shown, and in FIG. 21, the release (clip), which would not be visible per se in this longitudinal section, is shown rotated by 45°, FIG. 22 shows a section along line XXII—XXII in FIG. 21, FIG. 23 shows a section along line XXIII—XXIII in FIG. 21, in the section according to FIG. 23, the internal parts of the injection device are not shown, FIG. 24 is an enlarged detail of area XXIV in FIG. 19, FIG. 25 is an enlarged detail of area XXV in FIG. 20, FIG. 26 is a very schematic three-dimensional representation of the pushrod used in the third exemplary embodiment, in the form of a toothed rod, FIG. 27 shows only the upper and lower rows of teeth of the pushrod of FIG. 26, FIG. 28 shows only the left and right rows of teeth of the pushrod of FIG. 26, FIG. 29 is a schematic representation to explain the advancing process with an advance by a half a tooth space, FIG. 30 is an enlarged section shown in perspective, through the toothed rod shown in FIG. 31, where a part of the toothed rod is shown in a cutaway view in order to make the teeth more visible, and FIG. 31 is an enlarged three-dimensional representation of a toothed rod, where a part of the toothed rod is shown in a cutaway view in order to make the teeth more visible.

DETAILED DESCRIPTION

FIGS. 1 to 5 show the course of an injection process in a very schematic form.

FIG. 1 shows the injection device 10 in its rest position when the spring 11 is not cocked (analogous to the representations in FIGS. 8A & 8B, FIGS. 11A & 11B, and FIGS. 19 & 20). FIG. 2 shows the first part of the cocking process of the spring 11, in which a container (cartridge) 12 for the fluid to be injected moves from its proximal end position (FIG. 1) into its distal end position (FIG. 2) without a detent mechanism 46 already engaging in a detent opening 48 in a predetermined position (cocked position).

FIG. 3 shows the end of the cocking process, in which the spring 11 is fully cocked and the injection dosage is set. This corresponds to the representation in FIGS. 9A and 9B or to the representation in FIG. 21.

FIG. 4 shows the first phase of an injection, after an injection process is triggered, in which the needle is inserted, but no fluid is being injected yet.

Figure 9A:
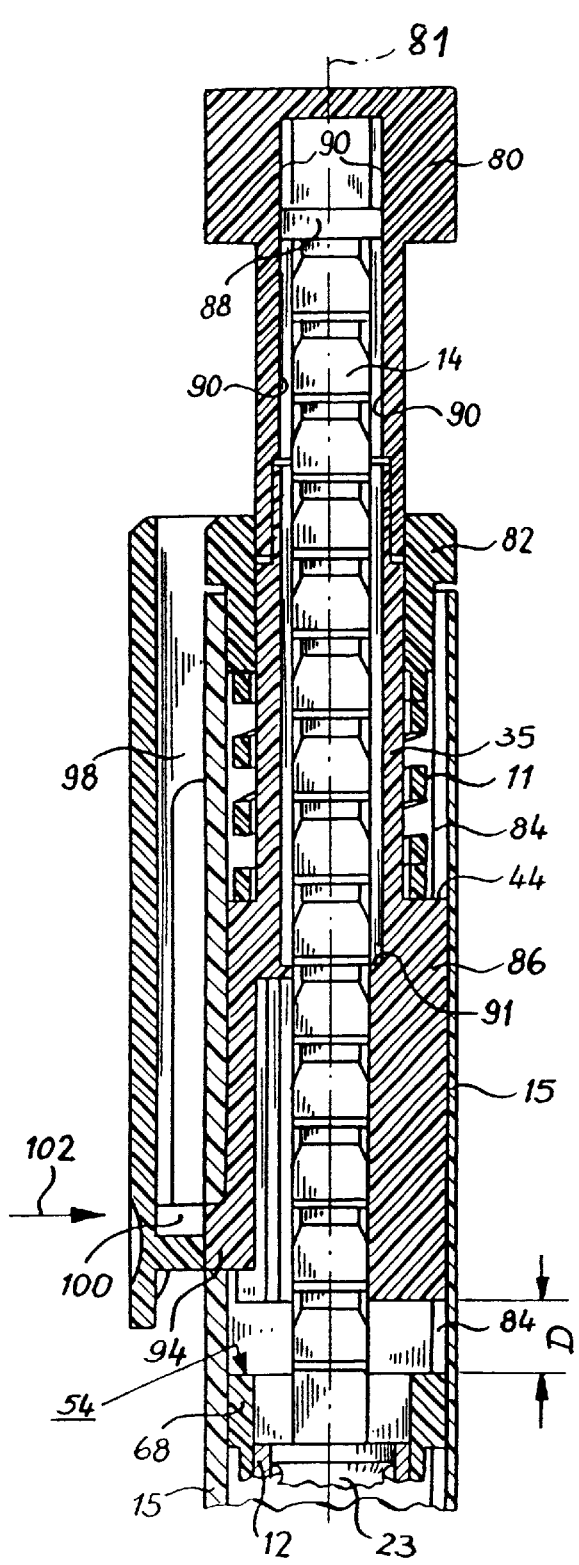

FIG. 5 shows the second phase of an injection, after the insertion of the needle, where FIG. 5 represents the state after the injection of the set fluid quantity. Here, the device is disposed once again in the rest position according to FIG. 1, but the pushrod 14, (which is formed as a toothed rod) is moved in the proximal direction by one tooth space in comparison to FIG. 1, corresponding to the injected quantity of fluid.

The injection device 10 has a housing 15, in which the container 12, received in a retainer 17, is arranged to be axially displaceable between a proximal end position (FIGS. 1, 4, & 5) and a distal end position (FIGS. 2 & 3). For this purpose, the retainer 17 has a radial projection 18 that can slide in a corresponding recess 20 of the housing 15 in the manner shown, between two axial abutment positions. The container 12 itself is fixed in the retainer 17 in a suitable manner. The container 12 is usually a glass ampoule on whose proximal end an injection needle 22 can be attached in the usual way depicted and in whose distal end a plunger 23 is slidably disposed. Ampoules (cartridges) of this kind are mass produced. If the plunger 23 is moved or shifted in the proximal direction, then fluid is expelled from the container 12 through the needle 22.

The terms "proximal" and "distal" are standard medical terminology; they are defined as follows: proximal: toward the patient, that is, to the left in FIGS. 1–5. distal: away from patient, that is, to the right in FIGS. 1–5.

Figure 10:
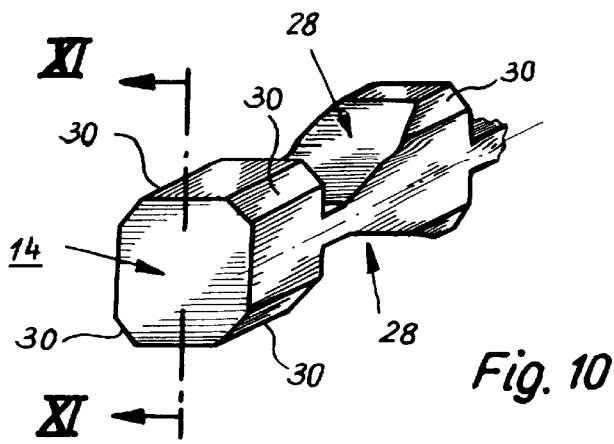

A detent mechanism in the form of a ratchet 27 loaded by a spring 26 (FIG. 6) is disposed as a first connecting device on a distal extension 25 of the retainer 17, and this detent mechanism is formed so that it can engage in a notch in the toothing 28 (FIG. 10) of the pushrod 14, whose preferred three dimensional form is shown in FIG. 10. This pushrod 14 has an essentially square cross section with beveled edges 30, which has teeth 28 on two opposing sides, as shown, and with its radially internal side, the ratchet 27 fits into the adjacent-facing notches in toothing 28 of the pushrod 14.

The radially outer side 32 (FIG. 6) of the ratchet 27 is controlled by the shape of the radially inner side of the housing 15. In the position according to FIGS. 1, 4, and 5, that is, the proximal end position of the container 12, this ratchet 27 can move radially outward, i.e., if the pushrod 14 here is moved in the proximal direction, the ratchet 27 is slid radially outward and according to FIG. 5, can slide into the next notch 28.

On the other hand, outside the proximal end position of the container 12, the inside of the housing 15 prevents the ratchet 27 from moving outward, as FIGS. 2 and 3 clearly show, and thus, in this position region, a direct drive connection is produced between the pushrod 14 and the retainer 17, which transmits a proximal movement of the pushrod 14 directly onto the container 12 and the needle 22. This drive connection is only interrupted when the container 12 has reached its proximal end position (FIGS. 1, 4, & 5), since only at this point can the ratchet 27 be moved radially outward in the manner described in detail above. This can also be described as link control or cam control of the ratchet 27.

It should be emphasized here that there are many potential variants of the detent mechanism for engaging in the notches of toothing 28. These are usually elastically deflectable parts whose elastic deflection is blocked outside of the proximal end position, that is, one is dealing with a path-dependent or position-dependent control of this elastic deflectability, which is naturally possible in a multitude of different forms.

The pushrod 14 is surrounded by a drive mechanism 35, formed here, for example, in the form of a tube that is disposed around the pushrod 14 and is used to drive it via a second connecting device. To this end, a detent mechanism is provided in an axial extension 36 of the drive mechanism 35 in the form of a radially movable, spring-loaded ratchet 38 which is formed in exactly the same way as the ratchet 27 shown in FIG. 6, that is, it can be shifted outwardly, counter to the force of a spring. As shown, the ratchet 38 engages in one of the notches of toothing 28 of pushrod 14, specifically on the upper side as shown in FIG. 1, while ratchet 27 on the lower side in FIG. 1 engages in one of the notches of toothing 28 of the pushrod 14. (This is the reason why teeth or notches are provided on different sides of the pushrod 14, preferably on two opposite sides.)

The radially outer end 40 (FIG. 2) of the ratchet 38 is controlled by the opposing inside 42 (FIG. 1) of the housing 15. As a comparison of FIGS. 1 and 2 shows, in the proximal end position range, a radial movement of the ratchet 38 is blocked, i.e. in this region, a movement of the drive mechanism 35 in both directions is completely transmitted to the pushrod 14.

When the position in FIG. 2 is reached, the retainer 17 with the container 12 is disposed in its distal end position by the projection 18 being in abutment against the distal end 20*d* (FIG. 5) of the housing recess 20. Starting from this point, the radial movement of the ratchet 38 is no longer blocked since from here on, the inside 42 of the housing 15 has a larger diameter. Therefore, after this, the ratchet 38 can slide past one tooth of the pushrod 14 into the next tooth notch, as shown in FIG. 3, and can engage there.

Since the cocking spring 11 is disposed between the distal end of the housing 15 and a shoulder 44 (FIG. 1) of the drive mechanism 35, it is compressed when the drive mechanism 35 is displaced in the distal direction, and when the cocked position is reached, a detent mechanism 46, located on drive mechanism 35, engages in the recess 48 of the housing 15 and locks the drive mechanism 35 in the position of FIG. 3. This is the position before an injection. Here, the needle 22 is disposed in the housing 15 so that it cannot be seen by the user, which relieves him of pre-injection anxiety. The retainer 17 is retained in this position in the housing 15 because it is connected to the pushrod 14 by the ratchet 27, and because for its part, pushrod 14 is secured against undesired axial movements relative to the drive mechanism 35 by means of ratchet 38, which rests against pushrod 14 with elastic bias. For its part, the drive mechanism 35 is locked into housing 15 by detent element 46.

FIG. 7 shows one possible design of the detent element 46, which is disposed here so that it can move radially in a recess 50 of the drive mechanism 35 and is acted upon in the radially outward direction by a cocking spring 52. FIGS. 8 and 9 show another preferred embodiment of this detent element and this is described below.

In the position of FIG. 3, if an injection is triggered by pressing on the detent element 46 in the direction of the arrow 53, then the spring 11 slides the drive mechanism 35 in the proximal direction. This movement is transmitted directly to the pushrod 14 via the ratchet 40 and for its part, the pushrod 14 transmits this movement directly to the retainer 17 and the container 12 via the ratchet 27, which cannot move out of the way in a radially outward direction, so that the container 12 is displaced in the proximal direction and the needle 22 is inserted into the patent, as shown in FIG. 4.

FIG. 4 also shows that even when the container 12 reaches its proximal end position, where its projection 18 abuts against the proximal end 20*p* of the recess 20, the ratchet 27 comes into the range of the recess 20 on the inside of the housing 15, and consequently can now move out of the way in a radially outward direction, i.e. the pushrod 14 can continue its proximal movement and now moves the plunger 23 in the container 12 in the proximal direction by one tooth space of the pushrod 14, which expels a corresponding quantity of fluid from the container 12 and injects it. For example, the pushrod 14 may have 10 or 14 teeth, depending on the size of the desired injection dosage.

When after several injections, all of the fluid has been expelled from the container 12, then the injection device 10 is spent and is ready for recycling. With a pushrod 14 having 14 teeth, as shown, 14 injections with identical dosages can thus be administered and after being triggered, the process of injection occurs automatically and with excellent dosage precision since the actual injection only begins after needle 22 has been inserted.

FIGS. 8 to 13 show a preferred embodiment of the invention. Parts which are the same or function in the same manner as those in the preceding Figures are usually indicated by the same reference numerals and are then only briefly described or not described at all.

Figure 13:
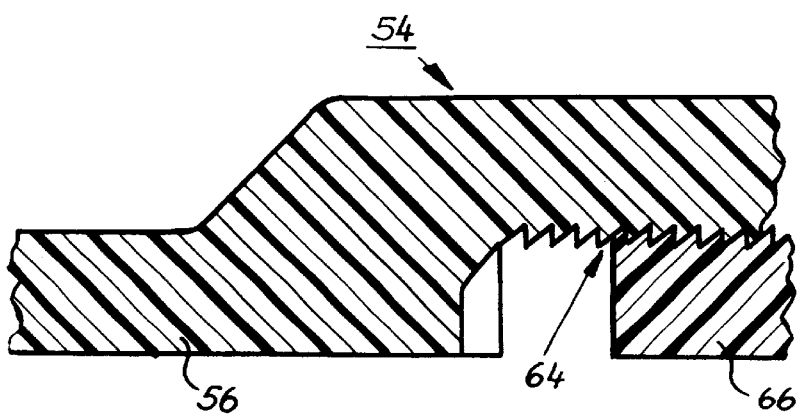

As FIGS. 8B and 13 show, the retainer 54 for the container 12 is formed here in two parts. It has a proximal section 56 whose proximal end has a thread 58 for screwing on a plastic part 60 attached to the needle 22, as clearly shown in FIG. 8B. On the distal end, this proximal section 56 has an enlargement 62, which has a micro-detent mechanism 64 on the inside, and into this, a distal section 66 is inserted, which also has a micro-detent on the outside of its proximal end, which engages in the micro-detent 64. The micro-detent 64 is only schematically represented in FIG. 13 because it preferably has a very fine tooth spacing of 0.1 mm, for example, which cannot be graphically represented. The sections 56 and 66 hold the container 12 (with its plunger 23) in the manner shown. This is a standard container and is made by several companies.

The retainer 54 is constructed of two sections 56 and 66 for the following reason: the container 12 and its filling quantity are subject to normal fluctuations so that in manufacture, the position of the plunger 23 relative to the retainer 54 always fluctuates between certain tolerance limits.

However, it is important that even before the first injection, the proximal end of the pushrod 14 rests directly against the plunger 23 so that, as FIG. 8 shows, if there is a gap between the plunger 23 and the proximal end of the pushrod 14 before the first injection, the first injection quantity is correspondingly reduced and the patient receives too little of the fluid he should have injected. Therefore, a gap of this kind has to be prevented.

This is carried out by virtue of the fact that, through the use of the micro-detent mechanism 64, the proximal section 56 of the retainer 54 is moved relative to the distal section 66 until the pushrod 23 rests without a gap against the proximal end of the pushrod 14. The micro-detent mechanism 64 maintains this connection between the sections 56 and 66.

The distal section 66 has a section 68 with a larger diameter with which it rests against a collar 70 on the inside of the housing 15 when in the proximal end position. This section 68 also guides the distal section 66 in a longitudinal groove 84 of the housing 15 and secures it against rotation.

Figure 9B:
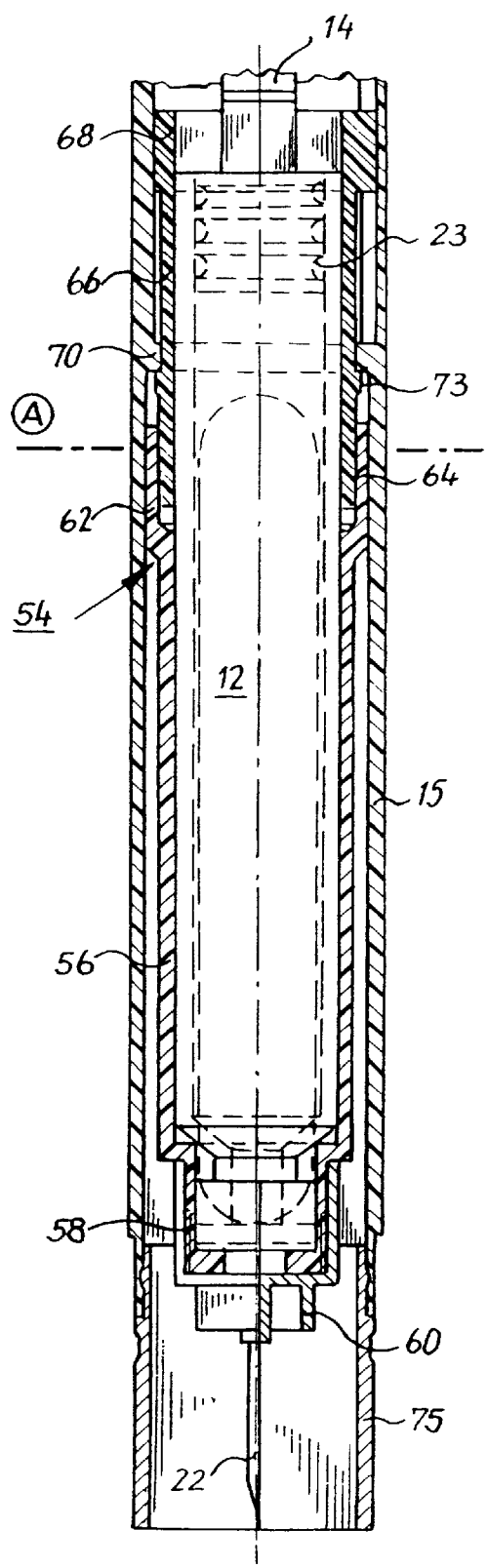

Furthermore, the distal section 66 has a stop 73 on its outside, with which it abuts against the collar 70 in the distal end position that is shown in FIG. 9B. The axial movement of the retainer 54 occurs as described in FIGS. 1 to 5, by position-dependent drive connection with the pushrod 14, which is described below in conjunction with FIGS. 11A and 11B. For clarity, the total stroke S of the retainer 54 is indicated in FIG. 8A.

In FIG. 8B, the housing 15 has a sleeve 75 for setting needle insertion depth and a protective cap 77 can be fitted onto this sleeve in the manner shown in order to protect the needle 22. As shown in FIG. 9B, in the cocked position, the needle 22 is disposed inside the sleeve 75.

It should furthermore be emphasized that in the rest position, the drive mechanism 35 rests with its proximal end against the distal end of the retainer 54, and is biased against it by the cocking spring 11, as shown in FIG. 8A. (In FIG. 8B, this is not shown.) When adjusting the micro-detent mechanism 64 as mentioned, this makes it possible to press against the proximal section 56 of the retainer 54 in the distal direction with a force K (on the left in FIG. 8A) and as a result, to reduce the gap between the plunger 23 and the proximal end of the pushrod 14 to zero.

FIG. 9A also shows that there is a distance D between the distal end of the retainer 54 and the proximal end of the drive mechanism 35 and this distance D corresponds to the quantity of fluid to be injected, i.e. here, the distance between two teeth 28.

In the embodiment according to FIGS. 8 to 13, the drive mechanism 35 has a pull knob or activating grippable member 80 for compressing the spring 11, which knob is secured to the drive mechanism 35 in the manner shown and forms one unit with it. (This knob is not shown in FIGS. 1 to 5.)

The longitudinal axis of the injection device 10 is labelled 81 in FIGS. 8 and 9. It should be noted that the representations of FIGS. 8 and 9 are very much enlarged, i.e. the entire device is approximately the size of an oversized fountain pen with a length of 16 to 17 cm, for example.

In the embodiment according to FIGS. 8 to 13, the cocking spring 11 is formed as an injection molded part (coil spring) made of plastic and it is preferably unitary with a part 82, which, as shown, constitutes the distal end of the housing 15 and is connected to it in the manner shown. The spring 11 rests with its proximal end against the shoulder 44 of the drive mechanism 35. The latter is guided in a corresponding cylindrical recess of the part 82, as shown in FIGS. 8A and 9A. Furthermore, it is guided with a radial enlargement 86 in the longitudinal groove 84 of the housing 15 so that it cannot rotate in the housing 15.

Likewise, the pushrod 14 is guided with an enlargement 88 on its distal end in two longitudinal grooves 90 on the inside of the drive member 35 or the knob 80 connected to it. These longitudinal grooves 90 extend to a point 91. If the enlargement 88 reaches this point 91, then the pushrod 14 cannot be slid further out of the drive member 35, and as a result, the actuation step shown in FIG. 3 is blocked, i.e. the device can no longer be brought into the cocked position shown in FIG. 3. As a result, the user knows that no further injection is possible.

For locking in the cocked position, the drive mechanism 35 has a detent hook 94 that can be elastically deflected inward, which is formed, as shown, as being of one piece with the drive mechanism 35 and like it, is formed of a resilient plastic material. In the position of FIG. 8A, it rests elastically against the inside of the housing 15 and in the cocked position of FIG. 9A, in which the spring 11 is cocked, it engages in the detent recess 48 (FIG. 8A) in the housing 15.

The injection device is triggered using a clip 98 that has a projection 100 which protrudes radially inward opposite from the detent recess 48. If the clip 98, which is formed of resilient synthetic material, is pressed inward in the direction of the arrow 102 (FIG. 9A), then it presses the detent hook 94 out of the detent recess 48 (FIG. 8A) and thus triggers an injection procedure, whose course has already been described in detail in conjunction with FIGS. 4 and 5. The cocking process has also already been described in detail in conjunction with FIGS. 1–3.

The clip 98 is preferably formed integrally with part 82 and spring 11, which greatly simplifies manufacture. The drive mechanism 35, the knob 80, the pushrod 14, and the housing 15 are preferably made of the same plastic as the part 82, the spring 11, and the clip 98, which simplifies the recycling of the injection device to an extraordinary degree since the entire distal part of the device can be recycled as a unit. Only the retainer 54 requires a transparent plastic so that the contents of the container 12 are externally visible (a window 105 in the housing 15 is indicated in FIG. 8B). Therefore, the retainer 54 must be disposed of separately, just as the container 12, naturally, which is usually made of glass.

In FIGS. 8, 9, and 11, a particular location in the injection device is labelled A for greater ease of orientation. Clearly the representations overlap in the central region.

Figures 11A, 11B:
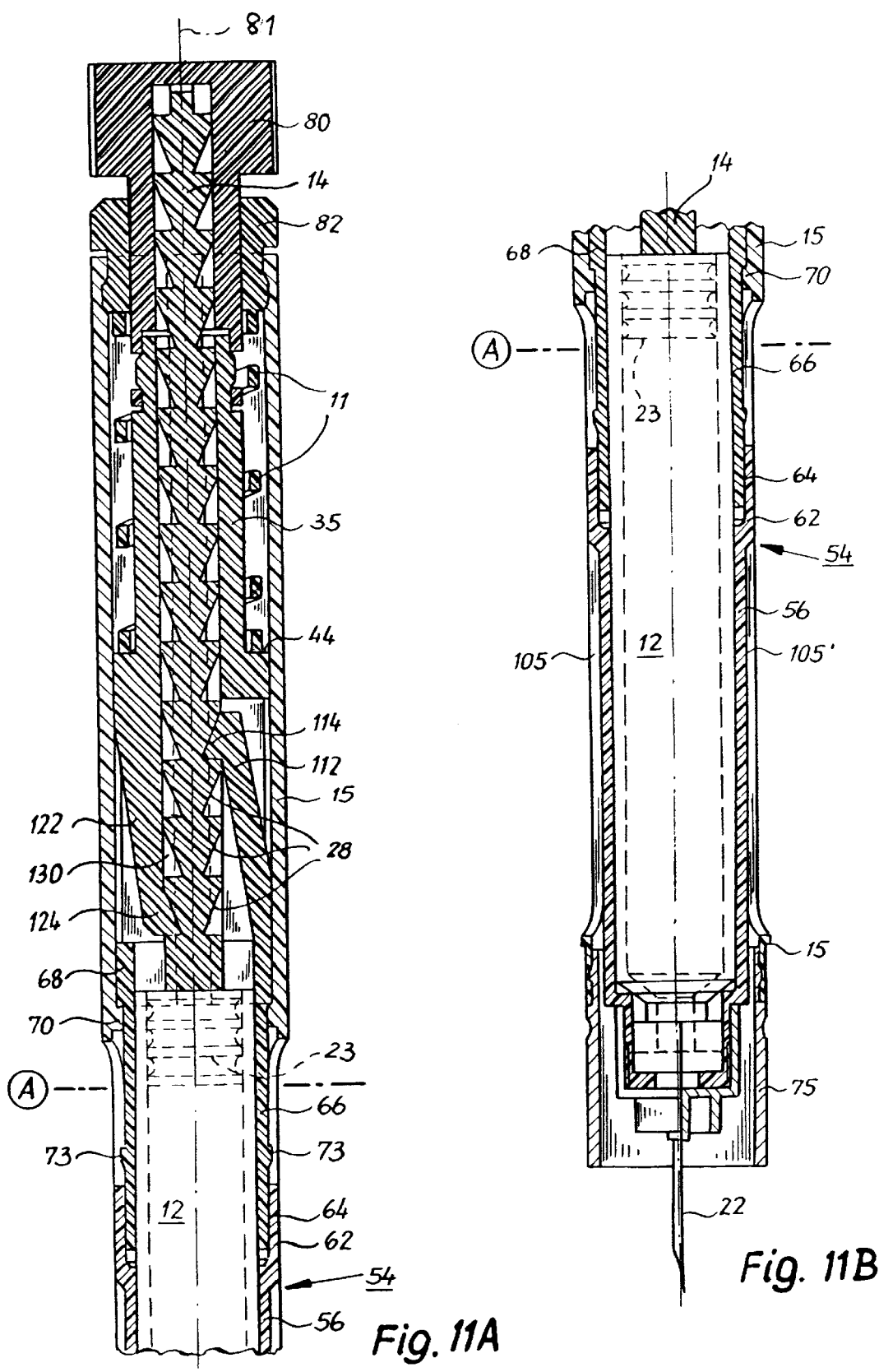

FIGS. 11A and 11B show a section viewed in the direction of line XI–XI in FIG. 10. In this representation, the injection device is disposed in a position according to FIGS. 8A and 8B, that is, the position after an injection, i.e. the needle 22 protrudes out from the sleeve 75. As shown in FIG. 11B, the housing 15 has two windows 105, 105' disposed opposite each other in the region of the cartridge 12, and since the parts of the retainer 54 are made of a transparent plastic, it is possible to see through these windows how much fluid is left in container 12.

Figure 12:
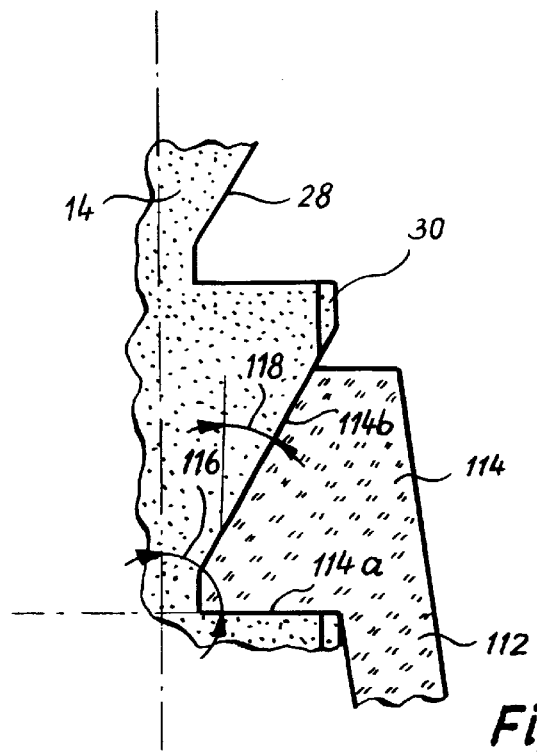

According to FIG. 11A, the distal section 66 of the retainer 54 is connected to an elastic extension 112 that runs diagonally inward in the distal direction at an angle of 10°, for example, and has a hook 114 on its free, distal end, which engages in a tooth space 28 of the pushrod 14. The extension 112 and hook 114 are used, in cooperation with the tooth spaces 28 of the pushrod 14, as a first connecting device that acts between the pushrod 14 and the retainer 54. As shown in FIG. 12, the proximal side 114a of the hook 114 runs at an angle 116 to the pushrod 14, and the distal, oblique side 114b of the hook 114 runs at an angle 118 to the pushrod 14. Angle 116 is on the order of 90° and angle 118 is preferably on the order of 15 to 30°. An angle of 23° turned out to be favorable in tests.

When the pushrod 14 moves in the distal direction, then it pulls the hook 114 and with it, the retainer 54, in the distal direction, which results in the position of the retainer 54 shown in FIG. 9B. Thus here, there is a positive engagement between the pushrod 14 and the hook 114.

In an injection procedure, if the pushrod 14 moves in the proximal direction, then the hook 114, whose side 114b is biassed against the pushrod 14, is likewise slid in the proximal direction, i.e. there is a partially positive and partially force-connected connection between the pushrod 14 and the hook 114, and the retainer 54 is moved in the proximal direction until reaching the position of FIG. 11B, in which section 68 of the retainer 54 rests against the collar 70 and a further proximal movement of the retainer 54 is prevented. If the pushrod 14 now moves further in the proximal direction, then the hook 114 slides out of the tooth space 28 and into the subsequent tooth space 28 of the pushrod 14, i.e. the first connecting device is disconnected after the needle 22 has been inserted so that now, the pushrod 14 can move the plunger 23 in the proximal direction. By means of this, the set fluid quantity is expelled from the container 12 and injected into the patient.

An elastic extension 122 protrudes obliquely inward from the drive mechanism 35 in the proximal direction and has a tip 124 on its free, proximal end fitted (adopted) to the teeth 28 that engages, as shown, in a tooth space 28 of the pushrod 14, on the left side in FIG. 11A. In cooperation with the tooth spaces 28, the extension 122 and the tip 124 function as a second connecting device that acts between the drive mechanism 35 and the pushrod 14.

Here, too, the schematic representation of FIG. 12 applies with regard to the angles and the preferred values of these angles, provided that the teeth and tooth spaces 28 are formed the same on both sides of the pushrod 14. (They may have different shapes and different angles if needed.) It is a good thing if the parts 114, 124 rest elastically, that is, with bias, against the pushrod 14 from opposite sides since then, it is not bent toward one side.

When the pull knob 80 is moved in the distal direction, then the tip 124 follows this movement and, since it is connected to the pushrod 14 by a frictional, non-positive connection, it displaces the pushrod 14 in the distal direction. In turn, the pushrod 14 pulls the retainer 54 in the distal direction via the hook 114 until the abutment 73 abuts against the collar 70. The retainer 54 travels through the path S shown in FIG. 8A.

When the part 73 abuts against the collar 70, a further distal movement of the retainer 54 is blocked, as well as a further distal displacement of the pushrod 14 (by the engagement of the hook 114 in a tooth space 28). If the pull knob 80 is now pulled further during the cocking movement, then the force-locking, non-positive connection between the tip 124 and the tooth space 28 is released and the tip 124 slides into the subsequent tooth space 130 of the pushrod 14. In this manner, the next injection dosage is set, which corresponds to the distance between two successive teeth or tooth spaces 28. The detent hook 94 engages in the detent recess 48, as already described.

When the injection device is triggered by pressing on the clip 98 (FIG. 9A), the spring 11 produces a force on the tip 124 in the proximal direction, which tip is now disposed in the tooth space 130. Because of the positive fit connection, the tip 124 displaces the pushrod 14 in the proximal direction, and this movement, as previously described, is transmitted to the retainer 54 through the force-locking, non-positive connection between pushrod 14 and hook 114, whereby the needle 22 is inserted. After the insertion, the force-locking, non-positive connection between the pushrod 14 and the hook 114 is interrupted and the pushrod 14 moves the plunger 23 by the preset distance, that is, the distance between two successive teeth or tooth spaces 28, and thus causes an injection of the set quantity of fluid.

It should be emphasized that the hook 114 and the tip 124 may also be prevented from moving radially outward in particular axial positions by corresponding parts (not shown) on the inside of the housing 15, as has been explained in great detail in conjunction with FIGS. 1 to 6 and can be immediately understood by one skilled in the art. However, in many cases, the embodiment described and shown in FIG. 11A is also sufficient for a reliable operation, provided that the biasing forces of the extensions 112, 122 and the angles of teeth 28 are correctly chosen. Tests have shown that the embodiment according to FIG. 11A functions in a completely satisfactory and reliable manner. In many instances, though, for safety reasons, cams will be provided in the housing, and, analogous to the embodiment according to FIGS. 1 to 6, will limit the radial movements of the extensions 112 and 122 in certain positions and in this way, prevent malfunctions with absolute certainty.

FIGS. 14 to 31 show a third embodiment of the invention in which the user can set the injection dosage in a simple manner and in which special steps are taken to permit an exact adjustment even of small injection dosages. Small dosages, for example 1 unit in the case of insulin, will require very small displacements when using commercially available cartridges, e.g. in the case of a known product, a path of the plunger in this cartridge of only 0.27 mm. The invention permits even this kind of small dosage quantity to be precisely adjusted and injected.

In this embodiment, the housing of the injection device 130 has a plurality of parts and a tubular housing part 132 as the main piece, whose shape can best be seen in FIG. 17, where on the right, this housing part 132 is shown in a partial cutaway view in order to show its interior.

Figure 14:
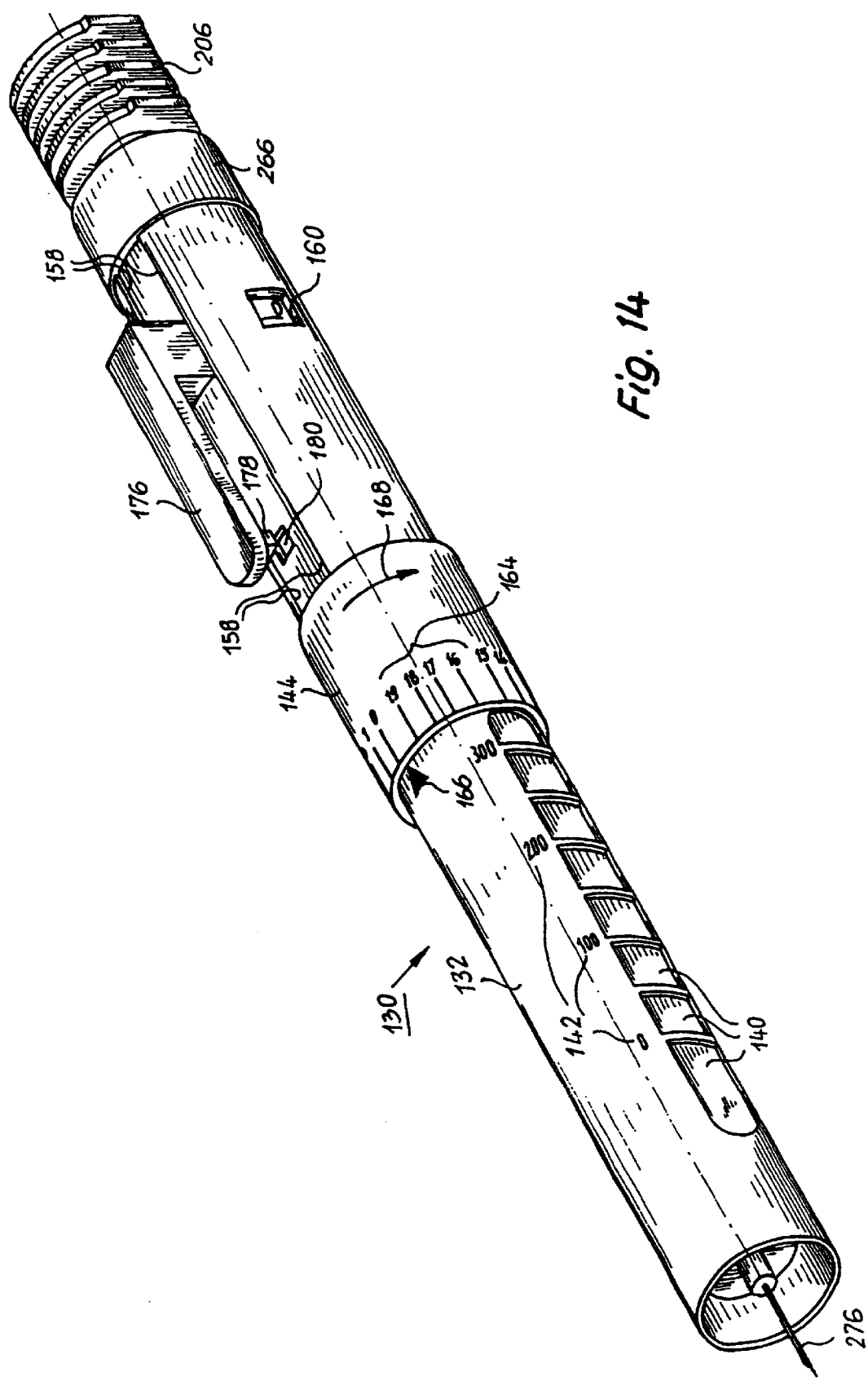

On the inside of its proximal section, the housing part 132 guides a transparent retainer 134 (FIG. 18) for a likewise standard type of transparent cartridge 136. On the inside, the housing part 132 has guide ribs (not shown) which guide elongated projections 137, 138 of the retainer 134 in the longitudinal direction so that this retainer cannot rotate in the proximal section of the tubular housing part 132. This proximal section has windows 140 on both sides through which one can see how much fluid is left in the cartridge 136. Numbers 142 on these windows permit a rough estimate of the remaining content of the cartridge 136. FIGS. 14 and 17 only show the windows 140 on one side of the tubular housing part 132; these windows are disposed symmetrically opposite from corresponding windows on the other side. A threaded sleeve 144 is attached to the tubular housing part 132, approximately in the center, and can be rotated, but cannot be displaced axially. As shown best in FIG. 15, the sleeve 144 has an internal thread 146 inside it, in the form of a fine pitch thread, and this engages with a corresponding external thread 148 of a housing part 150, whose shape is shown best in FIG. 17 and which can be shifted longitudinally in the housing part 132, for the purpose of adjusting the dosage.

According to FIG. 17, in its distal region, the tubular housing part 132 has a relatively wide longitudinal groove 152 on the bottom (with regard to FIG. 17), which has a rectangular window 154, whose shape is shown clearly in FIG. 17, approximately in the center of the housing part 132. The external thread 148' (FIG. 17) of the housing part 150 protrudes radially outward through this window 154— through the wall of the tubular housing part 132—so that it can engage with the internal thread 146.

As further indicated in FIG. 17—in part with only dot-and-dash lines 156—on its distal end, the tubular housing part 132 has a longitudinal slot 158 extending from the distal end of this housing part almost to its center. The longitudinal slot 158 is disposed diametrically opposite the window 154 and is equal in width to it. The external thread 148 of the housing part 150 protrudes radially outward through the longitudinal slot 158 to engage with the internal thread 146 of the threaded sleeve 144.

Figure 15:
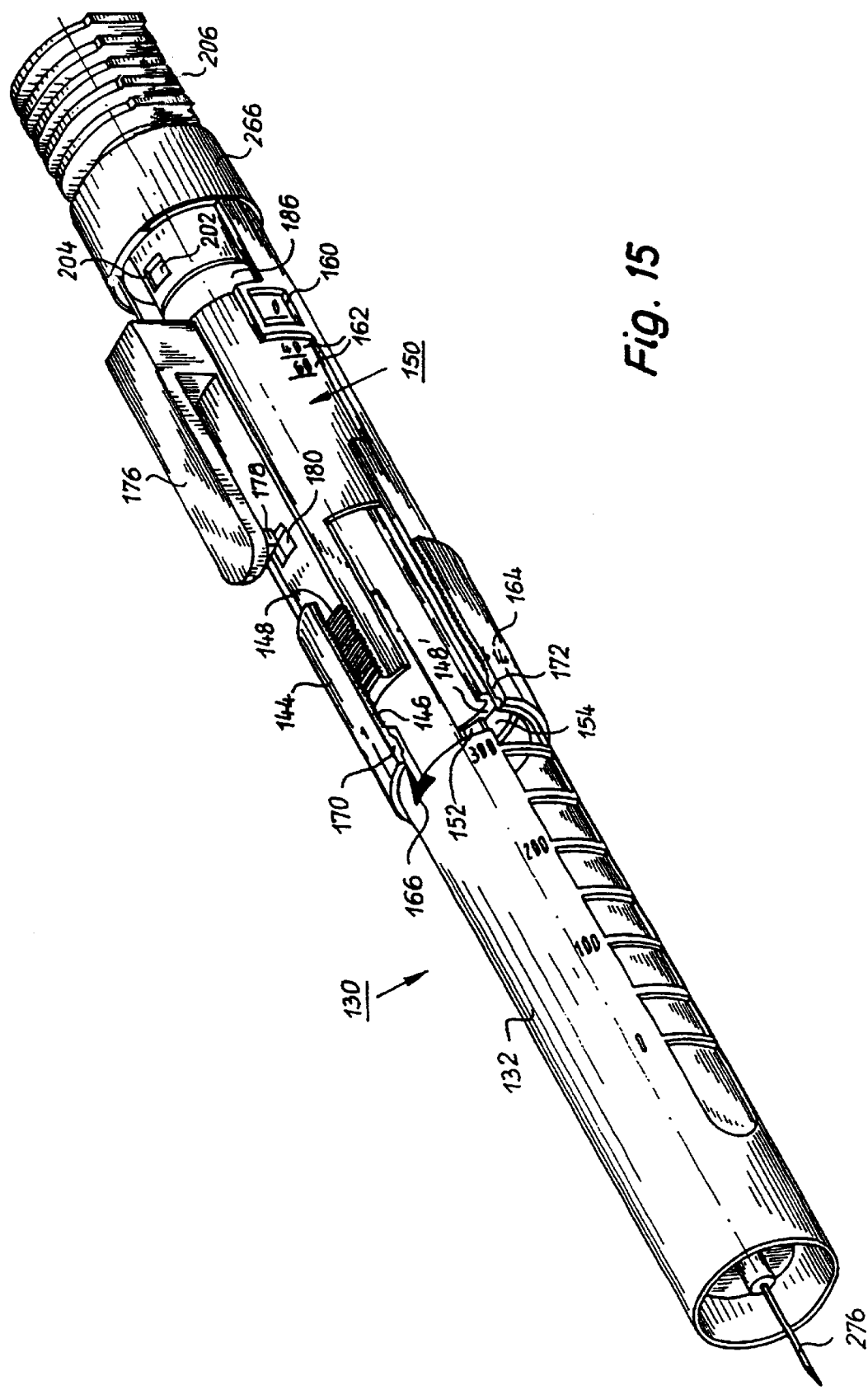

Furthermore, the tubular housing part 132 has a viewing window 160, through which an (approximate) dosage indication 162 can be read on the housing part 150, see FIG. 15. The micro-indication of dosage, e.g. from "0" to "19", is disposed on the threaded sleeve 144 in the form of indicia 164, and an associated indicator arrow 166 is disposed on the tubular housing part 132. The user thus adds the value 162 in the window 160, e.g. "0", to the value 164 indicated by the arrow 166, in order to obtain the current setting of the injection device 130, which is zero in FIG. 4. If he then rotates the sleeve 144 three graduation marks in the direction of the arrow 168 (FIG. 14), then he has set a dosage of three units; he only has to change this setting if he wants to subsequently inject a different dosage.

If the desired dosage is for example always 3 units, then the threaded sleeve 144 can remain in this position. This is particularly advantageous for diabetics with poor eyesight since changing the setting of the threaded sleeve 144 is not necessary before an injection. Rather, such a patient only has to cock the device, place it at the desired spot on the body, and then trigger the injection, without concerning himself over the dosage.

If the dosage needs to be changed, then the threaded sleeve 144 must be correspondingly rotated, where a rotation in the direction of the arrow 164 increases the injection dosage and a rotation counter to the arrow 164 decreases the injection dosage.

As shown in FIG. 15, on its inside, the threaded sleeve 144 has an annular projection (collar) 170 that engages in an annular groove 172 complementary to it on the outside of the tubular housing part 132. As shown, the collar 170 and the annular groove 172 have beveled flanks so that the threaded sleeve 144 can simply be pressed upon the housing part 132 until its collar 170 engages in the annular groove 172. As a result, after being installed on the housing part 132, the threaded sleeve 144 can rotate on it, but cannot slide axially in relation to it.

The internal thread 146 of the threaded sleeve 144 is so long that it covers the window 154 (FIG. 17).

The housing part 150 can slide linearly in the tubular housing part 132, but cannot rotate relative to it; both parts together compose the housing of the injection device. The distal section 174 (FIG. 17) of the housing part 150 essentially has the shape of a tube with a cylindrical cross section, which has a clip 176 attached to its distal end, whose projection 178 serves to engage in a radial detent opening 180 of the housing part 150. If the housing part 150 is displaced linearly in relation to the housing part 132 (by rotation of the threaded sleeve 144), then the position of the detent opening 180 moves in relation to the housing part 132 and this permits an adjustment of the injection dosage: the more the detent opening 180 is displaced in the distal direction, the greater the injection dosage will become.

Figure 23:
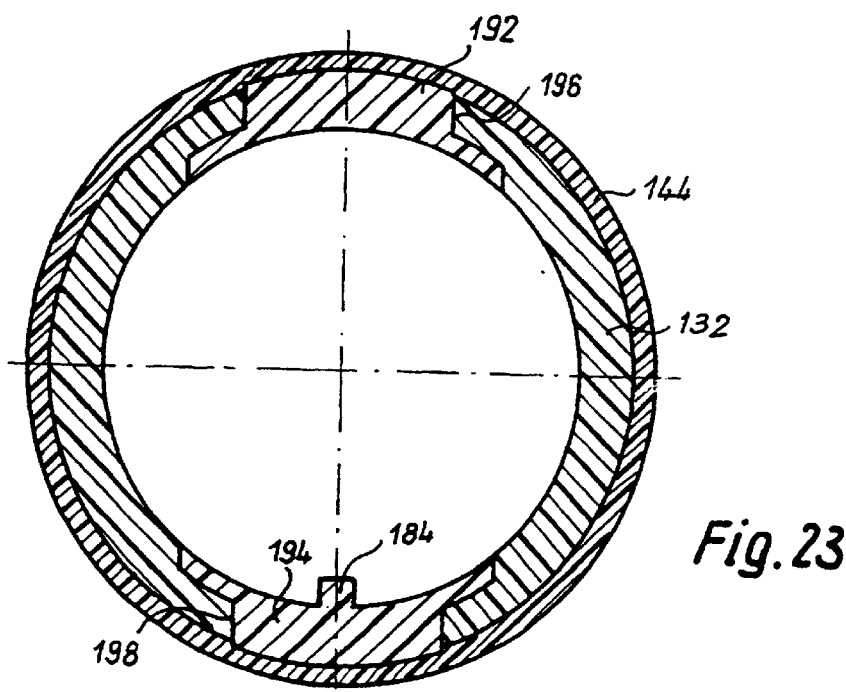

As best shown in FIGS. 17 and 23, on its inside, the housing part 150 has an axially extending guide projection 184 serving to guide a part 186 (FIG. 16), which is described below as an advancing part because in the case of a toothed rod 188 (FIGS. 16, 30, 31) that is guided in this advancing part, it causes an advancing movement in the proximal direction. For this, the advancing part 186 has a groove 190 (FIG. 16) that extends in the axial direction and is engaged by the guide projection 184.

On its proximal end, the housing part 150 has two diametrically opposed axial projections 192, 194, which can be elastically deflected toward each other during assembly. The upper projection 192 in FIG. 17 carries threaded section 148 and the lower section 194 carries threaded section 148'. On the upper projection 192, an elongated enlargement 196 extends, which is guided by the longitudinal slot 158 of the housing part 132 after assembly, and on the lower projection 194, an elongated enlargement 198 extends, which is guided in the groove 152 of the housing part 132 after assembly. As a result, when assembled, the housing part 150 is guided in the longitudinal direction in the housing part 132, as shown in FIGS. 14 and 15, and is connected to this by virtue of the fact that the internal thread 146 of the threaded sleeve 144 engages in the external thread sections 148 and 148' of the housing part 150.

Figure 22:
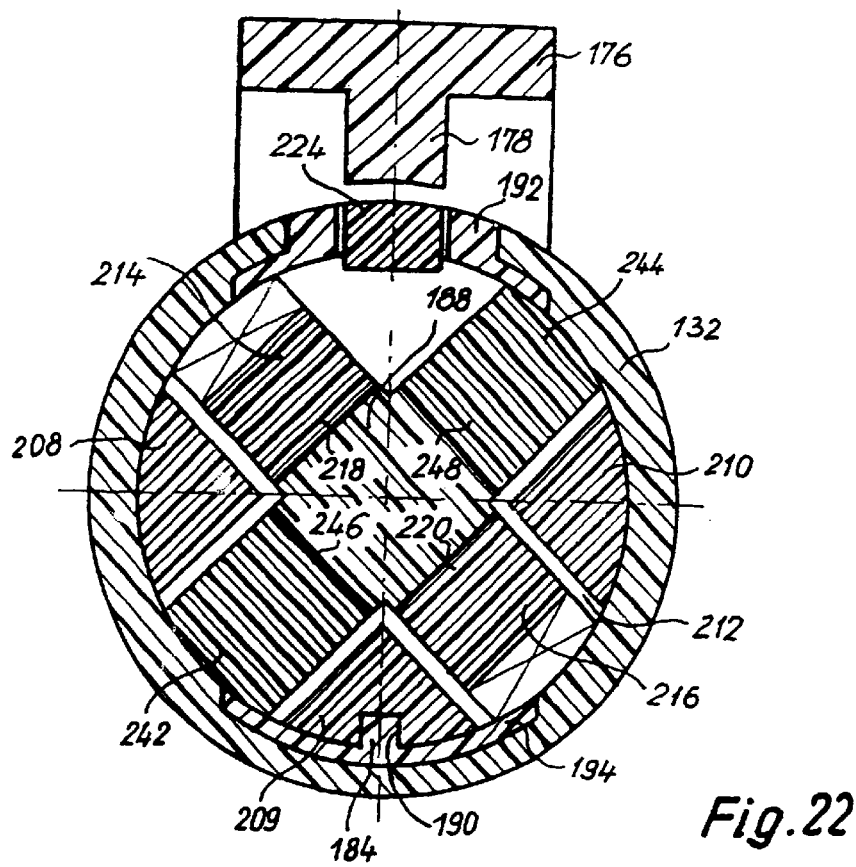
Figure 30:
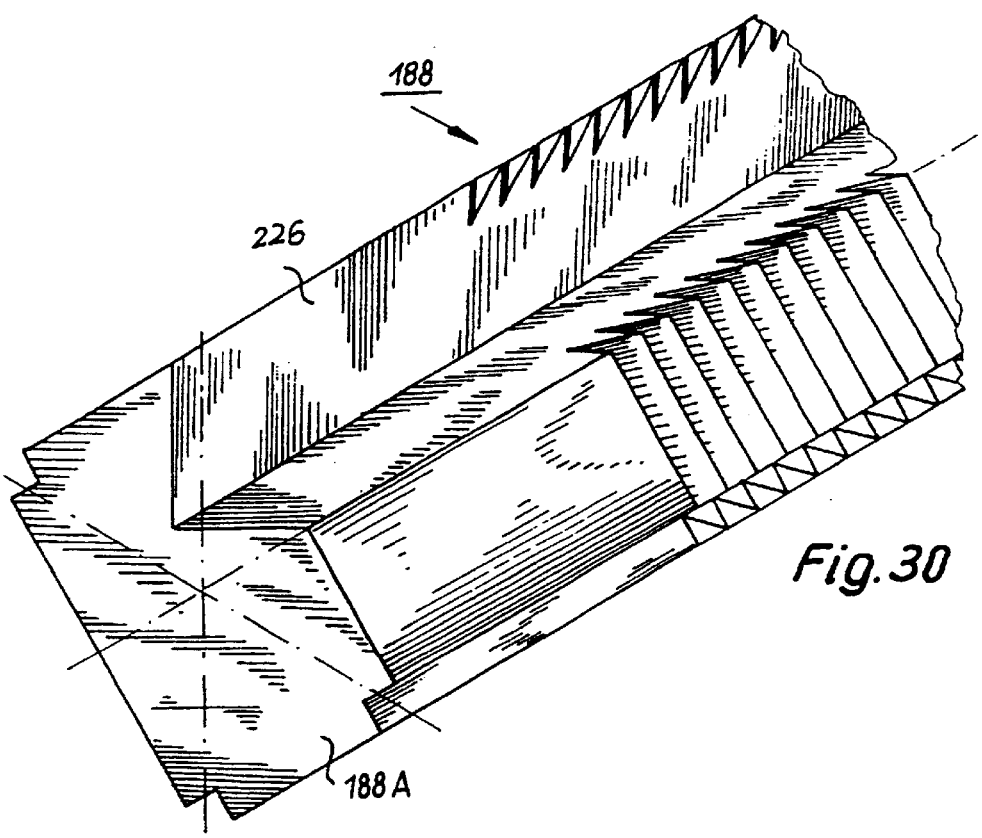
Figure 31:
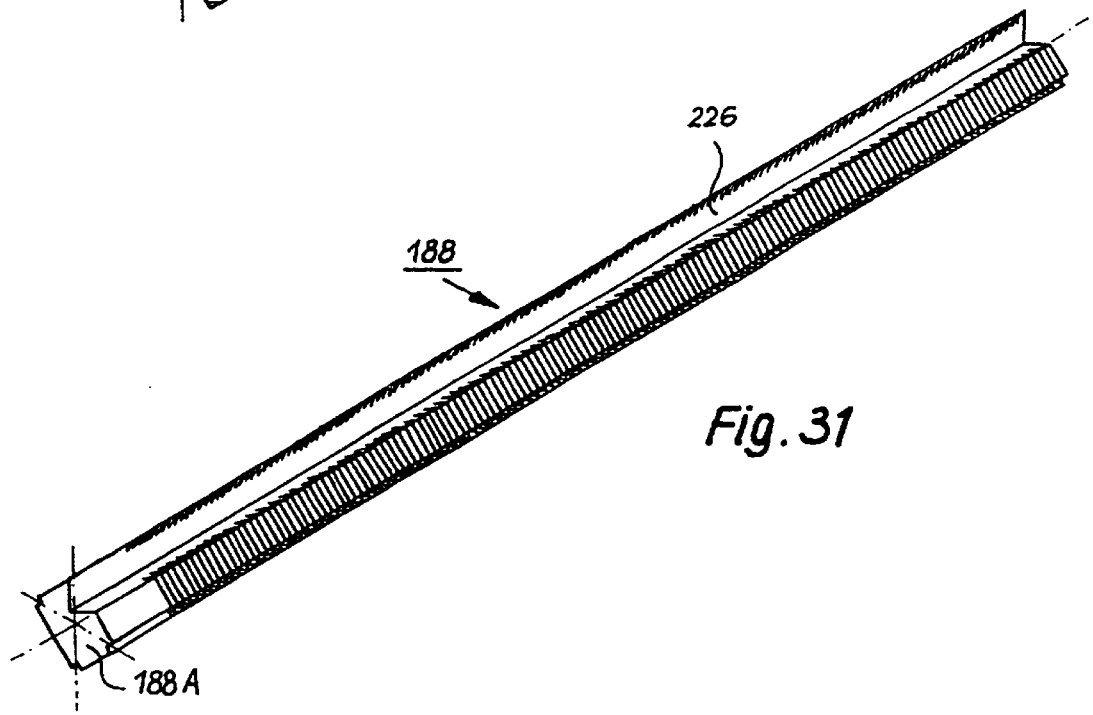

As shown in FIG. 16, in the region of its longitudinal axis, the advancing part 186 has a recess 200 with a square cross section, in which the toothed rod 188 is guided so that it can move longitudinally. This has an essentially square cross section as well, as shown in FIGS. 22, 30, and 31. On its distal end, the advancing part 186 has detent projections 202 on the top and bottom, which engage in corresponding detent recesses 204 of an actuation knob 206 upon assembly. (The advancing part 186 is shown in a partial cutaway view in FIG. 15, i.e. only its distal end is visible.)

The advancing part 186 has three guide parts 208, 209, 210; guide part 209 has a longitudinal groove 190, see FIG. 22. (In FIG. 16, the guide part 210 is not shown for the sake of clarity.) These guide parts slide along the inner wall 212 of the tubular housing part 132 and in this way, guide the advancing part 186 in it.

Furthermore, the advancing part 186 contains two elastic engaging members 214, 216 that are formed in the form of pliers and each have seven detent teeth 214', 216' on their free ends. These detent teeth are very small and therefore can only be shown well in the enlargement of FIG. 25.

Figure 25:
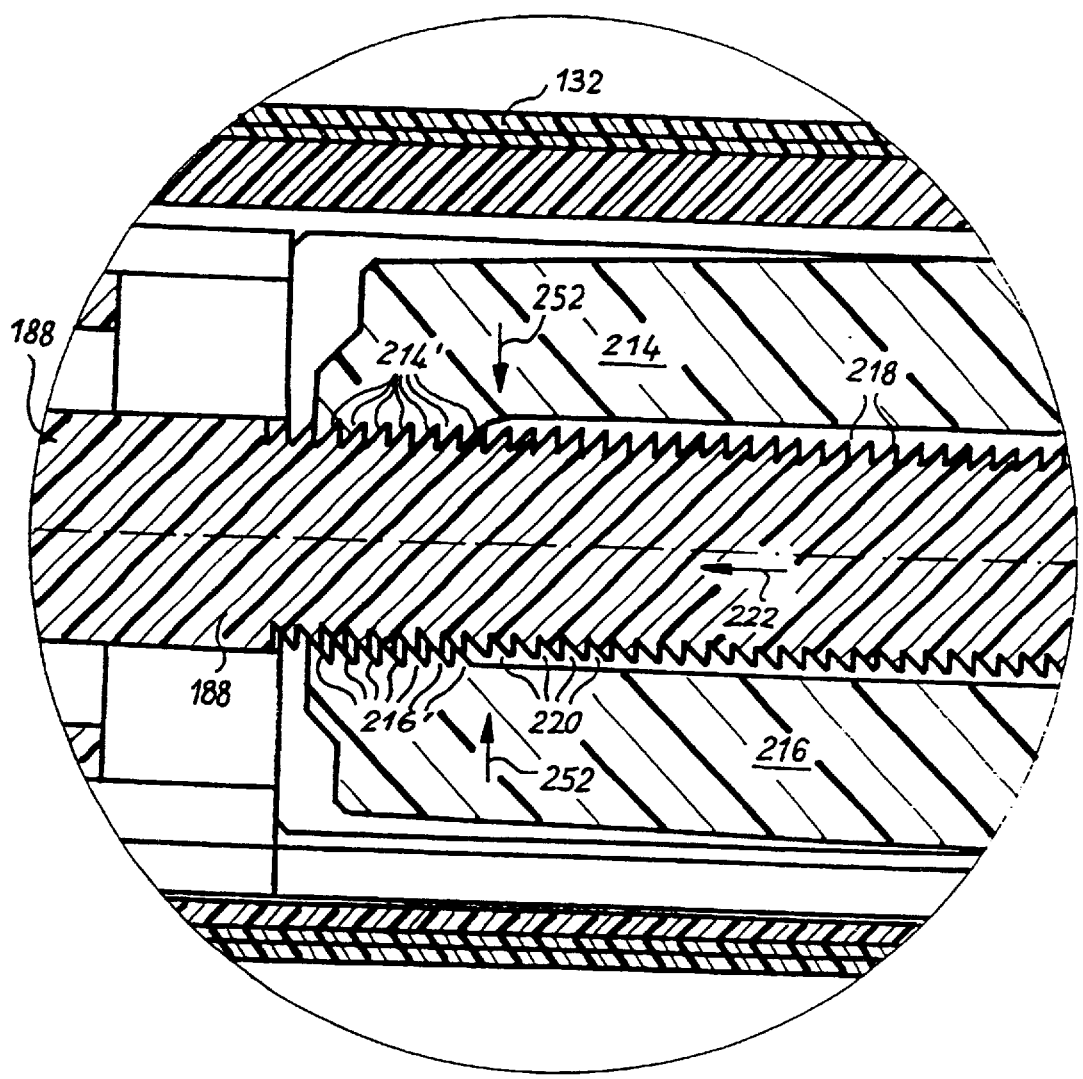

As shown in FIG. 25, the detent teeth 214', 216' are disposed directly opposite each other without being axially offset, while the teeth 218, 220 corresponding to them on the two sides of the toothed rod 188 that are effective here, are offset from each other by half a tooth space. Therefore, in this representation, the detent teeth 214' engage fully and with a biasing force into the teeth 218 of the toothed rod 188 while the detent teeth 216' engage only halfway and likewise with a bias force in the teeth 220 of the toothed rod 188. (Naturally, the teeth on the toothed rod 188 could alternatively be disposed opposite each other without being axially offset, and then the axial offset would be provided in the detent teeth 214', 216', but the form represented is the preferred one.)

As a result of the shape of the teeth, the toothed rod 188 can only move in the direction of the arrow 222, thus in the proximal direction, the engaging members 214, 216 then being elastically deflected radially outward. If the toothed rod 188 is moved by half a tooth space in the direction 222, then the teeth 216' engage fully with the teeth 220 of the toothed rod 188 and then the teeth 214' only engage the teeth 218 halfway. In this manner, an advance of half a tooth space can be executed, and here, a half a tooth space corresponds for example to 0.27 mm or one unit of the fluid to be injected.

Figure 29:
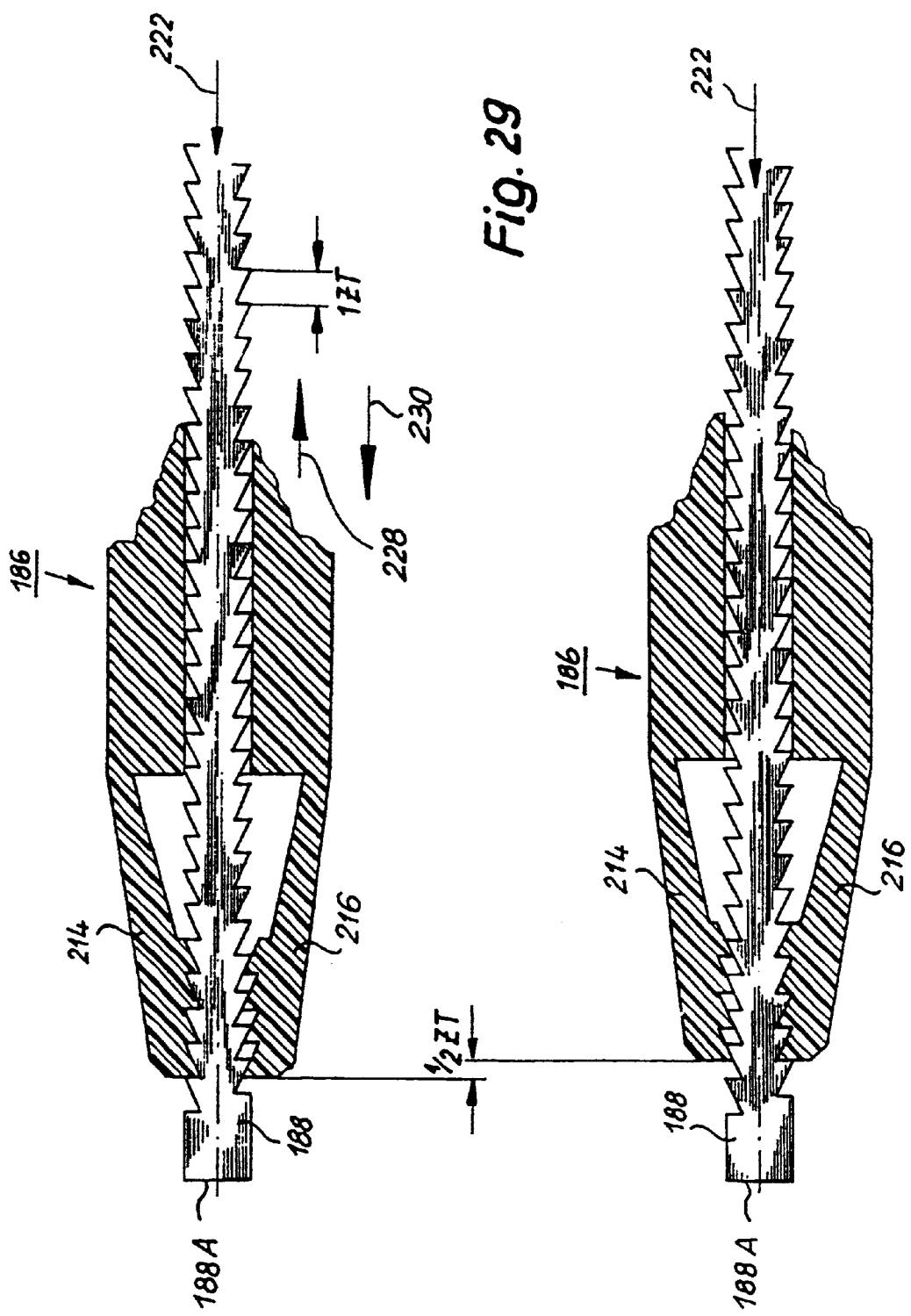

In a schematic representation, FIG. 29 shows an advancing procedure of the toothed rod 222 by half a tooth space, which is indicated in the drawing as "½ ZT". This occurs by virtue of the fact that the advancing part 186 first is displaced in the direction of an arrow 228 in the distal direction by half a tooth space, as shown in the lower part of FIG. 29, where in a manner further described below, the toothed rod 188 is held immobile and the teeth of the advancing part 186 are sliding onwards by half a tooth space, and by virtue of the fact that the advancing part 186 then is displaced in the proximal direction in the direction of an arrow 230, whereby the toothed rod 188 then is displaced in the proximal direction by half a tooth space.

Furthermore, the advancing part 186 also is provided with an elastic detent member 224 which engages in the detent opening 180 when the injection device 130 is cocked and which can be pressed out of the detent opening 180 by pressing on the clip 176 that serves as a trigger, in order to trigger an injection, as described in detail in FIGS. 8A and 9A. As shown in FIG. 22, the detent member 224 is disposed in the free space between two adjacent engaging members 214, 244, and is disposed opposite an edge of the toothed rod 188. In this manner, one succeeds in forming the injection device in a space-saving way, since in this manner, there is sufficient space available for the spring path of the detent member 224.

In order to make the teeth of the toothed rod 188 more visible, this is shown in FIGS. 16, 30, and 31 with a longitudinal groove 226. This longitudinal groove 226 does not really exist, as can be clearly seen from the section in FIG. 22. It is only there for improved visibility of the teeth.

Furthermore, the injection device 130 contains a retainer part 234, which is shown in three dimensional form in FIG. 17 and, in the assembled state, is connected to the retainer 134 (FIG. 18) using a detent process. The retainer part 234 has projections 236 on its outside whose function is explained below, and it has micro-detents 238 on its outside that cooperate with corresponding micro-detents 240 (FIGS. 20, 21) on the inside of the distal end of the retainer 134.

Figure 24:
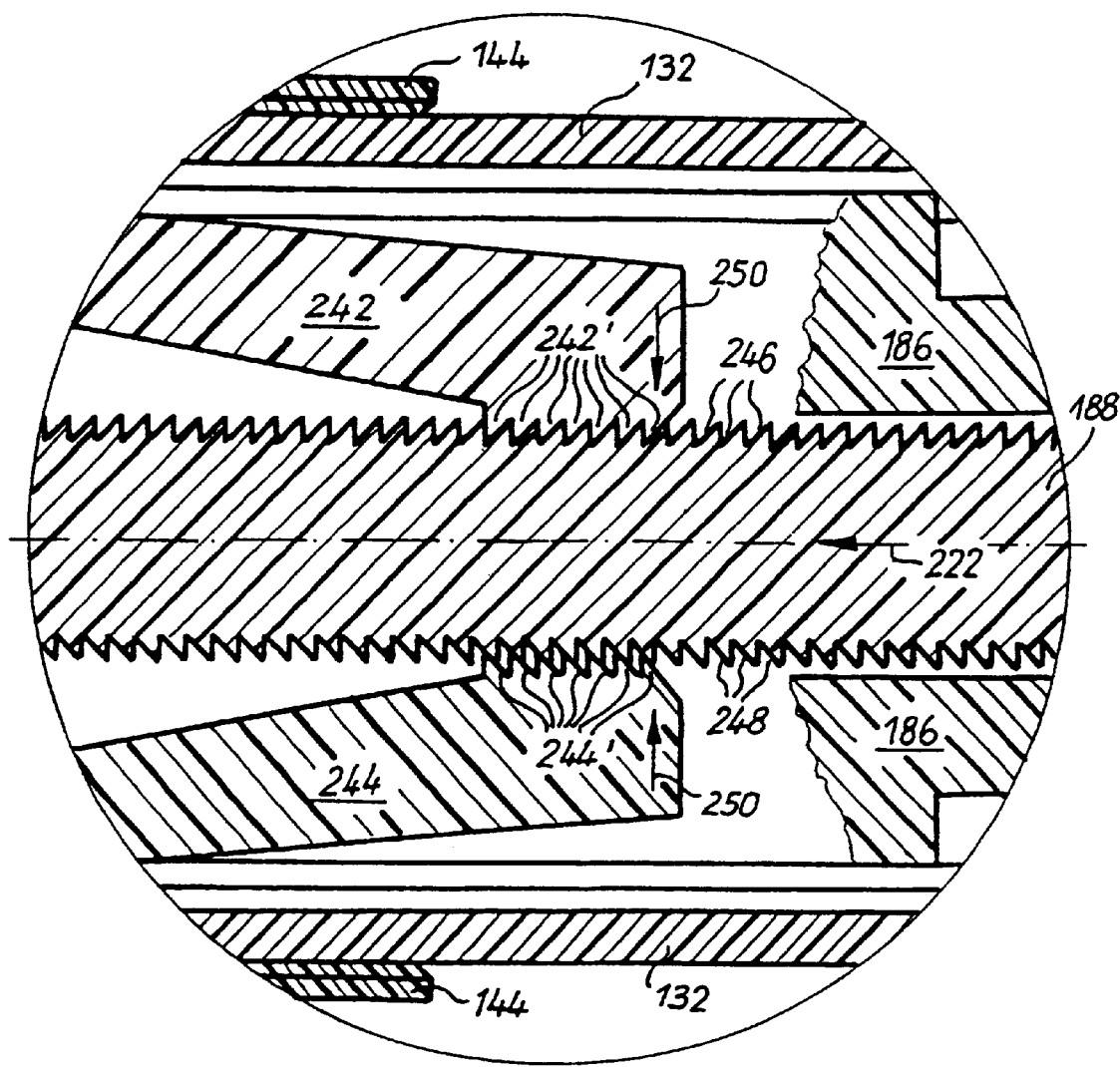

As can be seen best in FIGS. 19 and 24, on its distal end, the retainer 234 has two plier-like, elastically deflectable engaging members 242, 244 disposed opposite each other. The substantial enlargement in FIG. 24 shows that these engaging members are each provided with seven teeth 242' or 244', which are disposed opposite each other without being axially offset, analogous to the teeth 214' and 216' in FIG. 25. (Naturally, in principle, one single tooth or even half a tooth would be enough, but a greater number of teeth is preferable.)

The teeth 242' and 244' engage in corresponding teeth 246 or 248 on two opposite sides of the toothed rod 188. These teeth 246, 248 are offset in relation to each other by half a tooth space so that at all times only the teeth 242' fully engage the teeth 246, as shown in FIG. 24, or only the teeth 244' fully engage the teeth 248.

Also, the teeth 242', 244', 246, and 248 are so formed that they permit the toothed rod 188 to slide only in the proximal direction (arrow 222).

The engaging members 242, 244 are so formed that they rest against the toothed rod 188 with a bias force, as indicated with arrows 250 in FIG. 24. They are formed in the shape of a collet.

In the same manner, the engaging members 214, 216 of the advancing part 186 are so formed that they rest against the toothed rod 188 with bias, as shown with arrows 252 in FIG. 25.

The biasing forces 250, 252 increase the friction between the relevant engaging members and the toothed rod 188, which improves the function and assures a large degree of operational reliability. The fact that the initial biasing forces 250, 252 act symmetrically on the toothed rod 188, prevents it from being bent by these forces.

Figure 26:
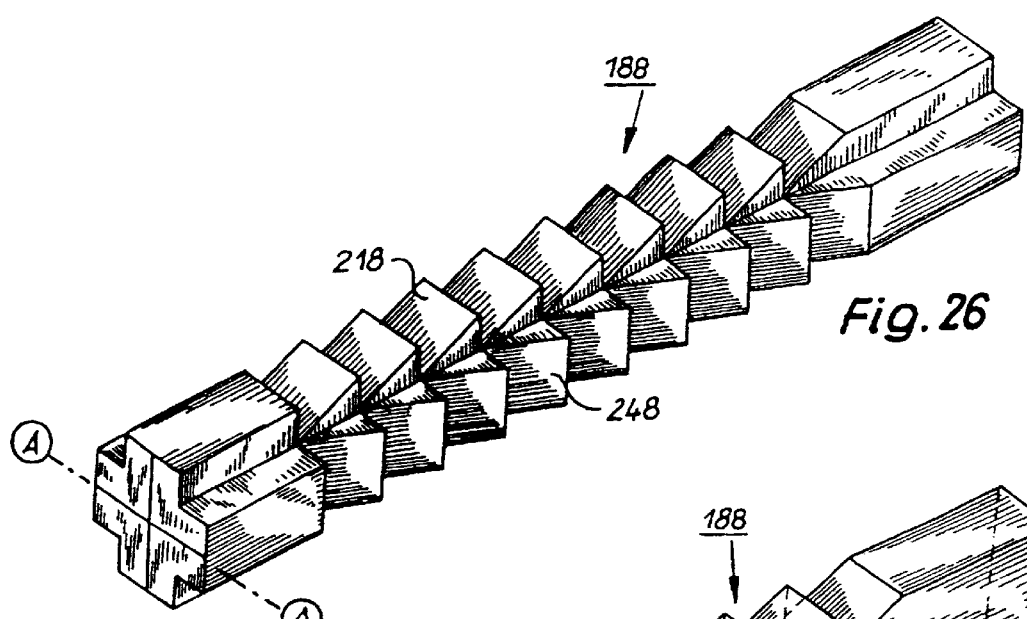
Figure 27:
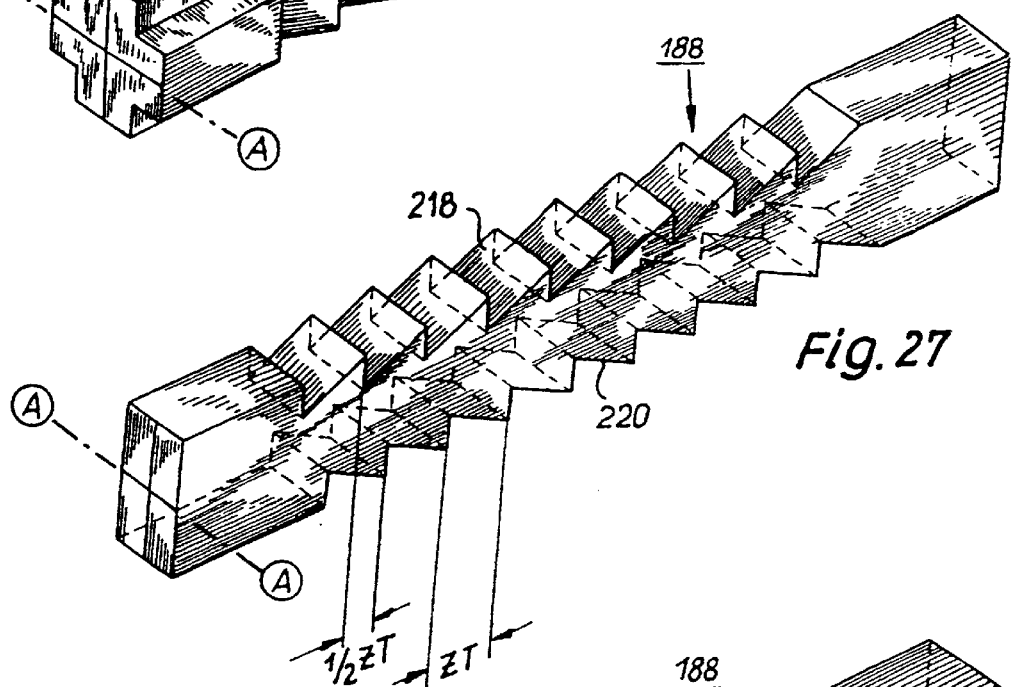
Figure 28:
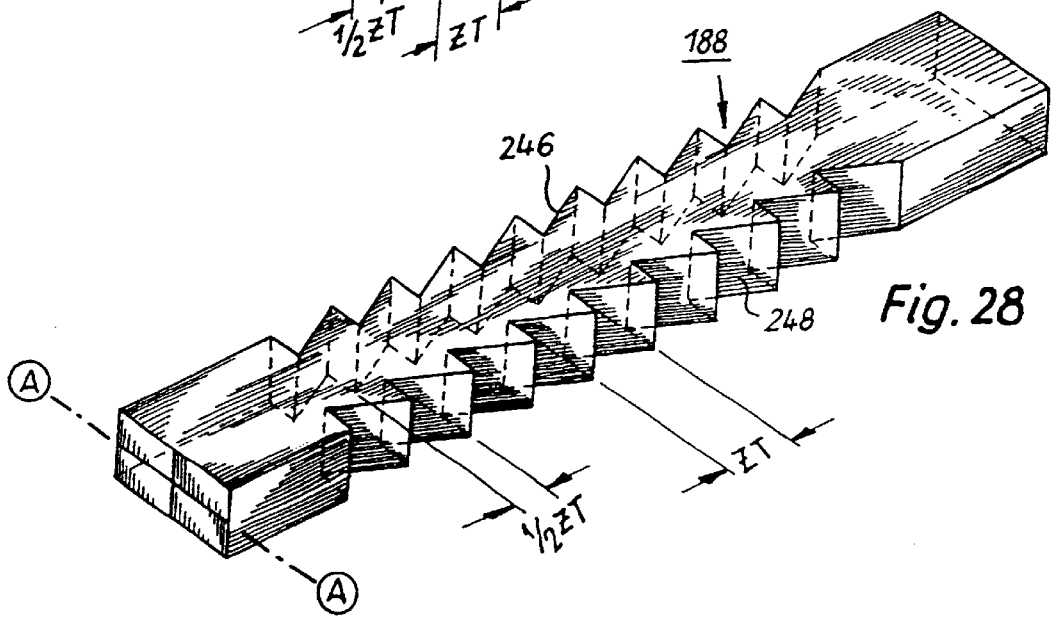

The schematic representations of FIGS. 26 to 28 will provide a clearer understanding of the structure of the toothed rod 188. The axis A—A is shown in all three Figures to make a simple orientation possible.

For greater ease of comprehension, FIG. 26 shows the toothed rod 188 in a three dimensional and substantially schematic form. Of the four rows of teeth, FIG. 26 shows only the two rows of teeth 218 and 248 which have the same tooth spacing and the same phase position, i.e. their spaces are disposed in the same plane.

FIG. 27 only shows the two opposite rows of teeth 218 and 220 which cooperate with the advancing part 186 and are offset in relation to each other by half a tooth space (½ ZT), which may also be called a phase shift of 180°.

FIG. 28 shows only the two opposite rows of teeth 246 and 248 that are likewise offset in relation to each other by half a tooth space (½ ZT), i.e. have a phase shift of 180°.

The rows of teeth 246 and 248 cooperate with the retainer part 234 (FIG. 17) and are used to drive it analogous to the driving of part 66 in FIG. 11A.

Assembly

First, the threaded sleeve 144 is lockingly engaged on the tubular housing part 132 in the manner previously described. Then, the part 234 is pushed into the housing part 132 from its distal end. With its detent projections 236, the part 234 slides over a corresponding inner detent bead 260 of the housing part 132. The detent projections 236 are shaped so that they permit this kind of a movement in the proximal direction, but not in the distal direction, since then, they act as abutments, as shown in FIG. 21. (In FIG. 21, the clip 176 that serves as a trigger is shown rotated by 45°, i.e. it would not actually be visible in this sectional view. FIG. 21 shows the cocked position for the injection of two units, corresponding to a single tooth spacing of the toothed rod 188.)

Then, the housing part 150 (FIG. 17) is pushed into the tubular housing part 132. The thread 148' engages in the window 154 in the housing part 132, and by rotating the threaded sleeve 144, the housing part 150 is brought into its zero position, which is indicated in the window 160. As a result, the housing is preassembled out of the parts 132, 144, and 150 and has the shape that can be seen in FIG. 14. This corresponds to the zero position, that is, the position for the injection of 0 units.

The advancing part 186 is now inserted into this housing from its distal end. The toothed rod 188 is inserted into the opening 200 of the advancing part 186 until the engaging members 214, 216 of the advancing part 186 engage in the first teeth on the proximal end of the toothed rod 188. This corresponds approximately to the position in FIG. 25, but displaced further to the left by one tooth.

Then, a cocking spring 262 (FIG. 16) is inserted from the distal end into the tubular housing part 132 until it abuts against the collar 264 of the advancing part 186, the advancing part 186 suitably being engaged lockingly with its elastically deflectable detent projection 224 in the detent opening 180. Then, a collar part 266 is fastened with adhesive or in detent fashion in the distal end of the tubular housing part 132. It serves as an abutment for the cocking spring 262.

In FIGS. 19 to 21, only the annular space 270 in which the cocking spring 262 will be disposed after installation, is shown since these drawings would have become very unclear if the cocking spring 262 had also been depicted there. With the exception of the cocking spring 262, all parts of the injection device 130 can be made of a suitable plastics material.

After the collar part 266 is fastened, the actuation knob 206 is fastened on the distal end of the advancing part 186, as described above (Parts 202, 204 in FIG. 16).

The mechanism is now assembled to a large degree, and the proximal end 188A (FIG. 29) of the toothed rod 188 is ready to actuate the plunger 272 (FIGS. 19 to 21) of the cartridge 136. The engaging members 214, 216 of the advancing part 186 and the engaging members 242, 244 of the retainer part 234 engage each other interdigitally, as clearly shown in the sectional view in FIG. 22. This is very similar to FIG. 11A, but cannot be shown in a longitudinal section. A comparison of FIGS. 19 and 20 shows this engagement in each other.

The detent connection with the detent member 224 is now released by pressing on the trigger 176 whereby—through the action of the spring 262—the toothed rod 188 assumes the position of FIGS. 19 and 20, and then the cartridge 136 is inserted into the tubular housing part 132 from the proximal end until its plunger or plunger 272 rests against the proximal end 188A of the toothed rod 188. Then the retainer 134 is inserted into the housing part 132, likewise from its proximal end. By means of a corresponding force, its internal micro-detent means 240 engages the micro-detent means 238 on the retainer part 234. The force required for this engagement is measured continuously. When this force increases because the plunger 272 of the cartridge 136 comes into contact against the proximal end 188A of the toothed rod 188, the detent connection process ends since at this point, the retainer 134 is disposed in the correct position on the retainer part 234.

The device is now complete and the patient can prepare it for use by screwing a needle 276 onto a thread 278 on the proximal end of the retainer 134. With its distal end, the needle 276 penetrates a rubber membrane 280 (FIG. 18) on the proximal end of the cartridge 136. (The needle 276 should be changed after each injection. It is attached just before an injection and until then, is kept in a sterile container.)

Operation

Before an injection, the desired dosage (e.g. 2 units) is set by rotating the threaded sleeve 144, as shown in FIG. 21. By this, the housing part 150 with its detent opening 180 is slid a corresponding distance in the distal direction relative to the housing part 132, e.g. at 2 units, by one tooth space of the toothed rod 188, corresponding for example to 0.54 mm. Therefore, this cannot be shown graphically in FIG. 21.

The cocking spring 262 (FIG. 16) is then cocked by pulling the actuating knob 206 in the distal direction, and the detent projection 224 is made to engage in the detent opening 180.

During this cocking movement, the engaging members 242, 244 (FIG. 19), which act like clamping jaws and carry the retainer 134 along, will pull the needle 276 into the tubular housing part 132, see FIG. 21. The projections 236 of the retainer part 234 (seen best in FIG. 17) come to a stop against the collar 260 in the housing part 132, and when this is the case, the teeth 214', 216' slide over the teeth 218, 220 of the toothed rod 188 by the one present tooth space, and thus set the dosage; then, the detent member 224, according to FIG. 21, engages in the recess 180.

After the release by means of the trigger 176, the compressed spring 262 pushes the toothed rod 188 in the proximal direction via the engaging members 214, 216, and by means of the engaging members 242, 244 of the retainer part 234, which act like clamping jaws, this movement is transferred directly to the needle 276 so that it is inserted into the tissue of the patient. The retainer part 234, with a radial projection 284 (FIG. 20), the abuts against the annular collar 260 on the inside of the housing part 132 and thus limits the insertion depth of the needle 276.

Since the toothed rod 188 still continues its movement in the proximal direction (arrow 222 in FIG. 24), it moves further in the direction of the arrow 222 in FIG. 24 by one tooth space relative to the engaging members 242, 244, (in this example, in which one tooth space has been preset as the injection dosage) whereby the corresponding quantity of fluid (2 units) is expelled from the cartridge 136 by the movement of the plunger 272. In the same way, it is also clearly possible to execute a movement of only half a tooth space, 1.5 tooth spaces, etc., and this is achieved by virtue of the fact that the devices according to FIGS. 24 and 25 are essentially identical.

In this manner, in the present embodiment, a dosage setting from 1 to 60 units is possible, which covers the requirements of actual use.

Naturally, there are many possible changes and modifications within the scope of the present invention. Thus, for example, instead of the offsetting of the teeth by half a tooth space, as shown in FIGS. 24 to 29, a device could be used with three rows of teeth, each of which is offset from the others by only ⅓ of a tooth space, where each row of teeth would then be associated with a corresponding engaging member. This and other kinds of modifications are easily produced by one skilled in the art and lie within the scope of the invention.

What is claimed is:

1. An injection device comprising
    a housing, a retainer axially movable within said housing for movement therein, during an injection, between a distal position and a proximal position thereof,
    a fluid container within said retainer,
    a plunger axially movable within said fluid container,
    a driving member axially displaceable within said housing,
    a toothed rod having a plurality of teeth arranged thereon in a longitudinal direction, said toothed rod being disposed in said housing for axial displacement therein and for acting on said plunger to express fluid from said fluid container during an injection,
    a first coupling device cooperating with teeth on the toothed rod, provided on said retainer, which normally locks said toothed rod to said retainer but permits relative axial movement therebetween while said retainer is not within a first predetermined axial position range inside said housing, and said toothed rod is moving in a predetermined axial rod movement direction, and
    a second coupling device, cooperating with teeth on the toothed rod, provided on said driving member, which normally locks said driving member to said toothed rod but permits relative axial movement therebetween while said driving member is not within a second predetermined axial position range inside said housing, and said driving member is moving in a predetermined driving member axial movement direction.

2. The injection device according to claim 1, wherein said second coupling device is so formed that the distal position of the retainer also constitutes a limit for distal movement of the pushrod.

3. The injection device according to claim 1, wherein, in the distal position of the retainer, the first coupling device is effective in both the proximal and the distal directions, but in the proximal position of the retainer, is only effective when the pushrod is moved in the distal direction.

4. The injection device according to claim 1, wherein
    in a proximal position range of the retainer, the second coupling device causes engagement between the driving member and the toothed rod during movement in both the proximal and the distal directions.

5. An injection device, comprising: a housing,
    a retainer axially movable within said housing for movement therein, during an injection, between a distal position and a proximal position thereof,
    a fluid container within said retainer,
    a plunger axially movable within said fluid container,
    a driving member axially displaceable within said housing,
    a toothed rod disposed in said housing for axial displacement therein and for acting on said plunger to express fluid from said fluid container during an injection,
    a first coupling device provided on said retainer and cooperating with teeth of said toothed rod, which normally locks said toothed rod to said retainer but permits relative axial movement therebetween while said retainer is not within a first predetermined axial position range inside said housing, and said toothed rod is moving in a predetermined axial rod movement direction, and a second coupling device provided on said driving member, and cooperating with teeth of said toothed rod, which normally locks said driving member to said toothed rod but permits relative axial movement therebetween while said driving member is not within a second determined axial position range inside said housing, and said driving member is moving in a predetermined driving member axial movement direction, and further comprising, coupled to the driving member, a detent mechanism, and a spring, acting upon the driving member in the proximal direction, and adapted to be compressed by moving the driving member and detent mechanism in the distal direction, said detent mechanism engaging against a fixed portion of said housing when a predetermined cocked position is reached.

6. The injection device according to claim 5, wherein the housing is formed with a radial opening therein, a clip, provided on the outside of the housing, is movable at said radial opening against the detent mechanism inside the housing, to release the detent mechanism and to thus trigger an injection process.

7. The injection device according to claim 1, wherein the driving member is connected to an actuating grippable member located on a distal portion of the device, for moving the driving member into its cocked position.

8. The injection device according to claim 1, wherein at least one of said coupling devices is formed as a frictional coupling device.

9. The injection device according to claim 1, wherein the first coupling device on the retainer comprises a member laterally movable into and out of engagement with the toothed rod.

10. The injection device according to claim 9, wherein the member connected to the retainer elastically engages, at least in the proximal end position of the retainer, with the pushrod, at least in the proximal end position of the container.

11. The injection device according to claim 9, wherein said first coupling device is axially movable together with said retainer.

12. The injection device according to claim 1, wherein the second coupling device has a shape complementary to that of the pushrod, for engagement with the pushrod and which, at least in the distal end position range of the retainer, engages elastically with the toothed rod.

13. The injection device according to claim 12, wherein, depending upon the position of the retainer, the second coupling device is prevented by a member secured to the housing from moving elastically away from the toothed rod.

14. The injection device according to claim 1, wherein a stop is provided on an inner surface of the housing for limiting movement of the toothed rod relative to the housing.

15. The injection device according to claim 1, wherein the length of the retainer is adjustable by forming the retainer of two interengaging sections.

16. The injection device according to claim 15, wherein the retainer has a proximal section and a distal section that are connected to each other by an adjustable connection which makes it possible to change the overall length of the retainer.

17. The injection device according to claim 1, wherein in its proximal position, the retainer rests with its distal end against a proximal end section of the driving member.

18. The injection device according to claim 1, wherein said first and second coupling devices each have a respective effectiveness which is a function of the respective position of the retainer.

19. An injection device having a housing, comprising an injection fluid container disposed in said housing, a toothed rod movable in relation to the housing to expel fluid from said container, a retainer serving to hold the container and movable in the housing between a proximal and a distal position, said retainer comprising a proximal retainer portion and a distal retainer portion, said retainer portions being axially displaceable relative to each other for permanently adjusting the length of said retainer.

20. The injection device according to claim 19, wherein, in a distal position range thereof, the retainer has abutment means, determining at least one end position thereof relative to the housing and wherein length adjustment of the retainer, by adjusting interengagement of sections thereof, is carried out relative to the abutment means so that, when the length of the retainer is changed, the position of the container relative to the toothed rod is changed.

21. The injection device according to claim 19, wherein the device for adjusting length has a micro-detent mechanism connecting a proximal section and a distal section of the retainer to each other in an adjustable way.

22. An injection device, comprising a housing, a retainer axially movable within said housing for movement therein, during an injection, between a distal position and a proximal position thereof, a fluid container within said retainer, a plunger axially movable within said fluid container, a driving member axially displaceable within said housing, a toothed rod disposed in said housing for axial displacement therein and for acting on said plunger to express fluid from said fluid container during an injection, a first coupling device provided on said retainer, and cooperating with teeth on said toothed rod, which normally locks said toothed rod to said retainer but permits relative axial movement therebetween while said retainer is not within a first predetermined axial position range inside said housing, and said toothed rod is moving in a predetermined axial rod movement direction, and a second coupling device provided on said driving member, and cooperating with teeth on said toothed rod, which normally locks said driving member to said toothed rod but permits relative axial movement therebetween while said driving member is not within a second predetermined axial position range inside said housing, and said driving member is moving in a predetermined driving member axial movement direction, and wherein the housing comprises two parts, and a device is provided for changing the relative position of the housing parts by linearly moving them relative to each other.

23. The injection device according to claim 22, wherein a first housing part is provided for guiding the retainer holding the injection fluid container and a second housing part, movable relative to said first housing part, comprises detent means for locking of a detent mechanism provided on the driving member.

24. The injection device according to claim 23, wherein the second housing part is formed with a radial opening therein, and a clip on the outside of the second housing part is provided for releasing, by actuation via said radial opening, the detent connection between the detent means and the detent mechanism inside said housing.

25. The injection device according to claim 22, wherein one of the housing parts movable relative to each other comprises a thread, and the other housing part comprises a threaded sleeve rotatable, but not axially movable, relative to the other housing part and being in engagement with said thread.

26. The injection device according to claim 22, further comprising a guide means for linearly guiding said housing parts that are movable relative to each other.

27. The injection device according to claim 22 wherein one of the housing parts is guided in the other.

28. The injection device according to claim 27, wherein an outer one of said housing parts is provided with at least one elongated recess, through which a part of an inner one of said housing parts protrudes radially.

29. The injection device according to claim 28, wherein the outwardly protruding part of the inner housing part is provided with an external thread which engages with the internal thread of a threaded sleeve disposed on the outer housing part, said sleeve being rotatable, but not axially movable, relative to said outer housing part.

30. The injection device according to claim 25, wherein the threads are small pitch threads.

31. The injection device according to claim 1, wherein the first coupling device comprises two engaging members provided with engaging elements adapted to engage corresponding rows of teeth of said pushrod.

32. The injection device according to claim 1, wherein the second coupling device has two engaging members provided with engaging elements adapted to engage corresponding rows of teeth on.

33. The injection device according to claim 31, wherein the toothed rod serving as a pushrod has a rectangular cross-section and, on a first pair of opposing sides, is provided with rows of teeth for engagement with the first coupling device, and, on the second pair of opposing sides, is provided with rows of teeth (246, 248) for engagement with the second coupling device.

34. The injection device according to claim 33, wherein said first coupling device and said second coupling device each comprise at least one engaging member, and said engaging members engage each other interdigitally.

35. The injection device according to claim 34, wherein one of the rows of teeth on the opposing sides of said toothed rod, and the engaging elements on engaging members which elastically engage these opposing rows of teeth, are offset from each other in an axial direction in order to permit, selectively, either:

a full engagement of an engaging element of the first of two elastic engaging members with the associated row of teeth of the toothed rod, while an engaging element of the second of two elastic engaging members is not in full engagement with its associated row of teeth but elastically applied thereagainst, or a full engagement of an engaging element of the second of two elastic engaging members with the associated row of teeth of the toothed rod, while the engaging element of the first of two elastic engaging members is not in full engagement with its associated row of teeth but elastically applied thereagainst, thus allowing adjustment of the injection device in steps smaller than one tooth division of the rows of teeth.

36. An injection device having a housing for receiving a container for a fluid to be injected, an actuating member, a toothed rod, having a longitudinal axis that is axially movable in response to said actuating member to expel fluid from a container disposed in the housing, and an axially movable part which engages against said toothed rod, wherein, in accordance with the, invention, the toothed rod, viewed in cross section transverse to its longitudinal axis, is polygonal;

at least two sides of a plurality of sides of said rod are each formed with a respective row of teeth, and said rows of teeth cooperate with said axially movable part;

said rows of teeth each have a predetermined tooth division, said axially movable part comprises a plurality of engaging members, and each engaging member is formed with at least one engaging element having a shape substantially complementary to a cooperating one of said rows of teeth and each engaging member is elastically biassed against said cooperating row of teeth, and wherein, in order to facilitate finer adjustment of an axial position of said toothed rod within said housing, there is an axial offset among at least one of the respective rows of teeth with respect to each other, and the engaging elements on the respective enagaging members with respect to each other.

37. The injection device of claim 36, wherein the rows of teeth of the toothed rod cooperating with said advancing part are disposed essentially symmetrically to a longitudinal axis of the toothed rod.

38. The injection device according to claim 36, wherein said advancing part is formed as a driving member for moving the container in the housing of the injection device.

39. The injection device according to claim 36, wherein the toothed rod has a rectangular cross-section, and said advancing part has two engaging members cooperating with rows of teeth on opposing sides of said toothed rod.

40. The injection device according to claim 5, wherein said spring is made of a plastic material.

41. The injection device according to claim 16, wherein the adjustable mechanism is a micro-detent mechanism.

42. The injection device according to claim 1, wherein said pushrod is provided with teeth on opposite sides, thereby forming a toothed rod.

43. The injection device according to claim 36, wherein said axially movable part is movable between a first orientation wherein a first one of said engaging members is fully engaged with a first one of said rows of teeth and a second one of said engaging members is elastically biassed against, but not fully engaged with, a second one of said rows of teeth, and a second orientation wherein said first one of said engaging members is elastically biassed against, but not fully engaged with, said first one of said rows of teeth and said second one of said engaging members is fully engaged with said second one of said rows of teeth whereby said axial position of said toothed rod within said housing can be adjusted more finely than a pitch spacing of said teeth.

* * * * *